US012377142B2

(12) United States Patent
Rittner et al.

(10) Patent No.: US 12,377,142 B2
(45) Date of Patent: Aug. 5, 2025

(54) RECOMBINANT PSEUDOCOWPOXVIRUS

(71) Applicant: TRANSGENE, Illkirch Gra

(56) References Cited

OTHER PUBLICATIONS

Chan et al., *Can NK cells be a therapeutic target in human cancer?*, 38 Eur. J. Immunol. 2964-2968 (2008).
Choi et al., *Novel chimeric parapoxvirus CF189 as an oncolytic immunotherapy in triple-negative breast cancer*, 163 Surgery 336-342 (2018).
Claudepierre et al., *Yeast Virus-Derived Stimulator of the Innate Immune System Augments the Efficacy of Virus Vector-Based Immunotherapy*, 88(10) Journal of Virology 5242-5255 (May 2014).
Erbs et al., *Modified vaccinia virus Ankara as a vector for suicide gene therapy*, 15 Cancer Gene Therapy 18-28 (2008).
Fend et al., *Intravenous Injection of MVA Virus Targets CD8+ Lymphocytes to Tumors to Control Tumor Growth upon Combinatorial Treatment with a TLR9 Agonist*, 2(12) Cancer Immunol. Res. 1163-1174 (2014).
Friedman-Kien et al., *Milker's Nodules: Isolation of a Poxvirus from a Human Case*, 140(3573) Science 1336-1336 (Jun. 21, 1963).
Gómez et al., *Clinical applications of attenuated MVA poxvirus strain*, 12(12) Expert Rev. Vaccines 1395-1416 (2013).
Hammond et al., *A synthetic vaccinia virus promoter with enhanced early and late activity*, 66 Journal of Virological Methods 135-138 (1997).
Hautaniemi et al., *The genome of pseudocowpoxvirus: comparison of a reindeer isolate and a reference strain*, 91 Journal of General Virology 1560-1576 (2010).
International Search Report issued (Jun. 12, 2019) in International Application No. PCT/EP2019/055744.
Kaufman et al., *Oncolytic viruses: a new class of immunotherapy drugs*, 14 Nature Review Drug Discovery Immunotherapy 642-662 (Sep. 2015).
Kumar et al., *A Poxvirus Bidirectional Promoter Element with Early/Late and Late Functions*, 179 Virology 151-158 (1990).
Laidlaw et al., *Comparison of the genome sequence of FP9, an attenuated, tissue culture-adapted European strain of Fowlpox virus, with those of virulent American and European viruses*, 85 Journal of General Virology 305-322 (2004).
Mia et al., *An optimized Protocol for Human M2 Macrophages using M-CSF and IL-4/IL-10/TGF-beta Yields a Dominant Immunosuppressive Phenotype*, 79 Scandinavian Journal of Immunology 305-314 (2014).
Movahedi et al., *Different Tumor Microenvironments Contain Functionally Distinct Subsets of Macrophages Derived from Ly6C(high) Monocytes*, 70(14) Cancer Research 5728-5739 (2010).
Parker et al., *Antitumour actions of interferons: implications for cancer therapy*. 16 Nature Reviews; Cancer 131-144 (Mar. 2016).
Quoix et al., *Therapeutic vaccination with TG4010 and first-line chemotherapy in advanced non-small-cell lung cancer: a controlled phase 2B trial*, 12(12) The Lancet Oncology 1125-1133 (Nov. 2011).
Remy-Ziller et al., *Sequential administration of MVA-based vaccines and PD-1/PD-L1-blocking antibodies confers measurable benefits on tumor growth and survival: Preclinical studies with MVA-BGal and MVA-MUC1 (TG4010) in a murine tumor model*, 14 Human Vaccines & Immunotherapeutics 140-145 (2018).
Rintoul et al., *ORFV: A Novel Oncolytic and Immune Stimulating Parapoxvirus Therapeutic*, 20(6) Molecular Therapy 1148-1157 (Jun. 2012).
Rittner et al., *Pseudocowpox virus (PCPV), a potent viral vector for both antigen-dependent and independent cancer immunotherapy*, XP002791666 1 page (Apr. 14, 2018); URL:https://www.transgene.fr/wp-content/uploads/2018/04/Poster-AACR-2018-PCPV.pdf [retrieved on May 24, 2019].
Rittner et al., *Pseudocowpox virus (PCPV), a potent viral vector for both antigen-dependent and independent cancer immunotherapy*, XP002791667 1 page (Nov. 7, 2018); URL:https://www.transgene.fr/wp-content/uploads/2018/11/Poster-SITC-2018-PCPV.pdf [retrieved on May 24, 2019].
Rooij et al., *Comparison of different prime-boost regimes with DNA and recombinant Orf virus based vaccines expressing glycoprotein D of pseudorabies virus in pigs*, 28 Vaccine 1808-1813 (2010).
Rziha et al., *Generation of recombinant parapoxviruses: nonessential genes suitable for insertion and expression of foreign genes*, 83 Journal of Biotechnology 137-145 (2000).
Schütze et al., *Inactivated parapoxvirus ovis activates canine blood phagocytes and T lymphocytes*, 137 Veterinary Microbiology 260-267 (2009).
Scott-Algara et al., *Changes to the Natural Killer Cell Repertoire after Therapeutic Hepatitis B DNA Vaccination*, 5(1):e8761 PLoS One 1-7 (Jan. 2010).
Shaul et al., *Neutrophils as active regulators of the immune system in the tumor microenvironment*, 102 Journal of Leukocyte Biology 343-349 (Aug. 2017).
Singel et al., *Neutrophils in the tumor microenvironment: trying to heal the wound that cannot heal*, 273 Immunological Reviews 329-343 (2016).
Tikkanen et al., *Recent isolates of parapoxvirus of Finnish reindeer (Rangifer tarandus tarandus) are closely related to bovine pseudocowpox virus*, 85 Journal of General Virology 1413-1418 (2004).
Von Buttlar et al., *Identification of Toll-Like Receptor 9 as Parapoxvirus Ovis-Sensing Receptor in Plasmacytoid Dendritic Cells*, 9(8):e106188 PLOS One 1-8 (Aug. 2014).
Wozniak et al., *Depletion of neutrophils in a protective model of pulmonary cryptococcosis results in increased IL-17A production by gamma/delta T cells*, 13(65) BMC Immunology 1-11 (2012).
Yamazaki et al., *Blockade of B7-H1 on Macrophages Suppresses $CD4_+T$ Cell Proliferation by Augmenting IFN-y-Induced Nitric Oxide Production*, 175 The Journal of Immunology 1586-1592 (2005).
Yuan et al., *The genome sequence of Sea-Island cotton (Gossypium barbadense) provides insights into the allopolyploidization and development of superior spinnable fibres*, 5(17662) Scientific Reports 1-16 (2015).
Zhao et al., *Specific qPCR assays for the detection of orf virus, pseudocowpox virus and bovine papular stomatitis virus*, 194 Journal of Virological Methods 229-234 (2013).
Zhou et al., *Macrophages from C3-deficient mice have impaired potency to stimulate alloreactive T cells*, 107(6) Blood 2461-2469 (Mar. 15, 2006).
Zitvogel et al., *Type 1 interferons in anticancer immunity*, 15 Nature Reviews; Immunology 405-414 (Jul. 2015).
Blomqvist et al., *An unusual presentation of pseudocowpox associated with an outbreak of pustular ulcerative vulvovaganitis in a Swedish dairy herd*, 30(2) J. Vet. Diagn. Invest.256-259 (Mar. 2018).
Müller et al., *Orf Virus-Based Vectors Preferentially Target Professional Antigen-Presenting Cells, Activate the STING Pathway and Induce Strong Antigen-Specific T Cell Responses*, 13 (Article 873351) Frontiers in Immunology (1-13) (May 2022).
Rall et al., *Recombinant Modified Vaccinia Virus Ankara (MVA) Vaccines Eciently Protect Cockatiels Against Parrot Bornavirus Infection and Proventricular Dilatation Disease*, 11 Viruses 1-14 (2019).
Ramos et al., *Pseudocowpox virus, a novel vector to enhance the therapeutic efficacy of antitumor vaccination*, 11 Clinical & Translational Immunology 1-23 (2022).
Ricordel et al., *Oncolytic properties of non-vaccinia poxviruses*, 9(89) Oncotarget 35891-35906 (2018).
Rohde et al., *New Orf Virus (Parapoxvirus) Recombinant Expressing H5 Hemagglutinin Protects Mice against H5N1 and H1N1 Influenza A Virus*, 8(12) PLoS One 1-13 (Dec. 2013).

\* cited by examiner

RECOMBINANT PSEUDOCOWPOXVIRUS

CROSS-REFERENCE TO RELATED APPLICATIONS

This application is a U.S. National Stage Application pursuant to 35 U.S.C. § 371 of International Patent Application PCT/EP2019/055744, filed on Mar. 7, 2019, and published as WO 2019/170820 on Sep. 12, 2019, which claims priority to European Patent Application No. 18305237.2, filed on Mar. 7, 2018, and European Patent Application No. 18306424.5, filed on Oct. 31, 2018, all of which are incorporated herein by reference in their entireties for all purposes.

TECHNICAL FIELD OF THE INVENTION

The present invention is in the field of viral immunotherapy. The invention provides new pseudocowpox (PCPV) viruses, in particular recombinant PCPV, composition thereof as well as their therapeutic use for preventing or treating diseases, and, notably, proliferative diseases like cancers and restenosis and infectious diseases. The present invention also provides methods for generating and amplifying such a PCPV and a method for eliciting or stimulating and/or re-orienting an immune response using such a PCPV. More specifically, the invention provides an alternative to the existing poxvirus vectors such as MVA (Modified Virus Ankara) and may be largely used for the therapeutic vaccination.

BACKGROUND ART

Immunotherapy seeks to boost the host's immune system to help the body to eradicate pathogens and abnormal cells. Widely used in traditional vaccination, immunotherapy is also being actively investigated as a potential modality for treating severe, chronic or life-threatening diseases in an attempt to stimulate specific and innate immune responses. A vast number of immunotherapeutics have been described in the literature for decades. In particular, several viral and non-viral vectors have now emerged, all of them having relative advantages and limits making them more appropriate to certain indications (see for example Cattaneo and Russell, 2017, PLOS Pathogens doi:10.1371/journalppat.1006190; Kaufman et al., 2015, Nature Reviews Drug Discovery 14: 642-661; Gomez et al., 2013 expert Rev Vaccines 12(12): 1395-1416). A huge number of immunotherapy platforms are being evaluated in clinical trials and the number of current clinical studies based on poxvirus therapy, whether oncolytic or not, reflects their interesting therapeutic potential. For example, recombinant vaccinia virus (VV)-based vectors are attractive candidates for their excellent safety profile and their capacity to combine robust cellular antigen-specific immune responses with a generalized stimulation of the innate immune system. TG4010 (or MVATG9931 with its research name) is a therapeutic cancer vaccine based on a modified vaccinia virus Ankara (MVA) coding for MUC1 tumor-associated antigen and human interleukin 2 (IL-2). TG4010, in combination with first-line standard of care chemotherapy in advanced metastatic non-small-cell lung cancer (NSCLC), demonstrated efficacy in two different randomized and controlled phase 2b clinical trials (Quoix et al., 2011, The Lancet Oncology 12(12): 1125-33).

Parapoxviruses represent different candidates that can be used in vector vaccines. Parapoxvirus belongs to the family Poxviridae and the subfamily Chordopoxvirinae. Parapoxviruses are commonly known as causative agents of dermal diseases in ruminants, leading to papular stomatitis and contagious pustular dermatitis, especially in the regions of the lips, nostrils, oral mucosa, and teats. Like other members of the Poxviridae family, parapoxvirus are relatively large and enveloped double-stranded DNA viruses with ovoid geometries that can infect vertebrates including a wide selection of mammals and humans. Parapoxviruses have a unique spiral coat that distinguishes them from other poxviruses.

As for poxviruses, viral replication of parapox is cytoplasmic. Entry into the host cell is achieved by attachment of the viral proteins to host glycosaminoglycans (GAGs) that mediates endocytosis of the virus into the host cell. Fusion with the plasma membrane permits to release the core into the host cytoplasm. Early genes are transcribed in the cytoplasm by viral RNA polymerase. Early expression begins at 30 minutes post-infection. Intermediate phase triggers genomic DNA replication at approximately 100 minutes post-infection. Late genes are then expressed from 140 min to 48 hours post-infection, producing all structural proteins. Assembly of progeny virions starts in cytoplasmic viral factories, producing a spherical immature particle. This virus particle matures into brick-shaped intracellular mature virion (IMV). IMV virion can be released upon cell lysis or can acquire a second double membrane from trans-Golgi and bud as external enveloped virion (EEV) host receptors, which mediates endocytosis. The virus exits the host cell by existing in occlusion bodies after cell death and remains infectious until it finds another host.

Replication-competent as well as inactivated Parapoxviruses are known for their immunomodulating properties (Schulze et al., 2009, Vet Microbiol. 137: 260-7). Parapoxvirus ovis (ORFV), the prototype species of the parapoxvirus genus, has been used successfully in veterinary medicine for increasing general resistance in animal chronically persistent viral infections (see e.g. U.S. Pat. No. 6,365,393; WO97/32029 and US2003-0013076) as well as in human medicine for treating HIV (WO2006/005529) and considered as oncolytic by some (Rintoul et al., 2012, Mol. Ther. 20(6): 1148-57). Various insertion sites were identified within the ORFV genome (WO97/37031). Notably, recombinant ORFV encoding canine disempter virus (CDV) antigen were used as vaccine against CDV (WO2012/01145) and pseudorabies virus in pigs (Rooij et al., 2010, Vaccine 28(7): 1808-13). Zylexis®, formerly known as Baypamune®, which is a preparation of chemically inactivated ORFV derived from strain D1701 is used for the prophylaxis and therapeutic treatment of infectious diseases and for preventing stress-induced diseases in animals. Inactivated ORFV was shown to induce plasmacytoid dendritic cells (pDC) probably through the engagement of a TLR-9 dependent pathway (Von Buttlar et al., 2014, PLOS One 9(8): e106188). More recently, Choi et al. (2017, Surgery, doi 10.1016/j.surg.2017.09.030) reported potent cytotoxic activities of a chimeric parapoxvirus in triple negative breast cancer (TNBC) tumors. Active replication of the chimeric ORF virus was detected in the tumor tissues 1 week after its injection and natural killer (NK) cell infiltration was observed in the periphery of virus treated tumor tissues.

There is clearly an important need to develop effective approaches for the treatment of life-threatening diseases such as cancers and infectious diseases. Indeed, diseased cells have evolved potent immunosuppressive mechanisms for eluding the immune system, posing a major obstacle to effective immunotherapy. Hence, triggering both innate and specific immune mechanisms may be key to successful development of more effective immunotherapeutics.

The present invention relates to using Parapoxvirus as a vector for the delivery of therapeutic genes. The inventors surprisingly discovered that Pseudocowpox virus (PCPV) offers remarkable advantages which makes it particularly appropriate for anti-cancer therapy considering its limited pathogenicity and immune modulating properties. The inventors discovered that PCPV provides a strong innate immune profile different from those of other poxviruses as evidenced by its ability to activate secretion of a number of cytokines and chemokines that stimulate immune effector cells at a level higher than conventional MVA and VV. Another member of Parapoxvirus genus, the bovine popular stomatitis virus (BPSV), showed similar effects in PBMCs as PCPV with a strong increase of secreted IFN-alpha in supernatants. Moreover, increased CD86 expression in human in vitro-derived M2 type macrophages suggests a role of PCPV in reprogramming M2 macrophages towards a less suppressive phenotype. Finally, a recombinant PCPV virus engineered to express tumor-associated antigens (TAA) was shown particularly effective to control tumor growth and enhance survival in a syngenic animal model. The combination of PCPV with an anti-PD1 antibody showed statistically significant improvement of tumor control in a "two tumor" model.

Due to the improved immunogenic properties exhibited by the PCPV and BPSV viruses, one may anticipate that parapoxvirus may be successfully used as an alternative to other viral therapies for treating or preventing proliferative diseases such as cancer and infectious diseases (e.g. chronic HBV). Thus, PCPV or BPSV is a candidate for a therapeutic vaccine which could have effects on the tumor environment.

SUMMARY OF THE INVENTION

One aspect of the invention relates to a pseudocowpoxvirus (PCPV) wherein said PCPV comprises at least one foreign nucleic acid inserted in its genome.

In one embodiment, said PCPV is obtained from the wild-type TJS strain as identified by ATCC reference number ATCC VR-634™ or from a virus strain of the same or similar name or functional fragments and variants thereof.

In another embodiment, the PCPV may be further defective for a viral function encoded by the PCPV genome and preferably for a non-essential viral function and, more preferably for a viral gene function encoded at the insertion site of said foreign nucleic acid.

In a further embodiment, said foreign nucleic acid encodes a polypeptide selected from the group consisting of polypeptides that compensate for defective or deficient proteins in a subject, polypeptides that act through toxic effects to limit or remove diseased cells from the body such as suicide gene products; polypeptides capable of potentiating anti-tumor efficacy such as armed gene products; and polypeptides capable of inducing or activating an immune response such as immunostimulatory and antigenic polypeptides. Preferably, the immunostimulatory polypeptide is selected from the group consisting of cytokines, such as interleukins, chemokines, interferons, tumor necrosis factor, colony-stimulating factors, APC-exposed proteins, polypeptides having an anti-angiogenic effect and polypeptides that affect the regulation of cell surface receptors such as agonists or antagonists of immune checkpoints with a specific preference for an interleukin or a colony-stimulating factor and, in particular GM-CSF or an agonist OX40-directed antibody. Also preferred is a cancer antigen such as the MUC-1 antigen, a viral antigenic polypeptide such as the HPV-16 E7 antigens or HBV antigens.

In still a further embodiment, the at least one foreign nucleic acid is operably linked to suitable regulatory elements for expression in a desired host cell or subject.

In an additional embodiment, the at least one foreign nucleic acid is inserted in the VEGF locus.

In another aspect, the present invention further provides a method for generating the PCPV of the invention, by homologous recombination between a transfer plasmid comprising the foreign nucleic acid flanked in 5' and 3' with PCPV sequences respectively present upstream and downstream the insertion site and a PCPV genome, wherein said method comprises a step of generating said transfer plasmid and a step of introducing said transfer plasmid into a suitable host cell, notably together with a PCPV virus comprising the flanking sequence present in the transfer plasmid.

In one embodiment, the site of insertion of the at least one foreign nucleic acid in the PCPV genome is in a viral gene, with a preference for a non-essential viral gene, in an intergenic region, in a portion of the PCPV genome which does not encode gene products or in a duplicated locus and, preferably, the VEGF locus.

In one embodiment, the transfer plasmid further comprises one or more selection and/or detectable gene to facilitate identification of the recombinant PCPV with a preference for the selection GPT gene and/or a detectable gene encoding GFP, e-GFP or mCherry.

In a further aspect, the present invention further relates to a method for amplifying the PCPV of the invention or generated by the method of the invention, comprising the steps of a) preparing a producer cell line, b) transfecting or infecting the prepared producer cell line, c) culturing the transfected or infected producer cell line under suitable conditions so as to allow the production of the virus, d) recovering the produced virus from the culture of said producer cell line and optionally e) purifying said recovered virus.

In still a further aspect, the present invention relates to a composition comprising a therapeutically effective amount of the PCPV of the invention or amplified by the method according to the invention and a pharmaceutically acceptable vehicle. Preferably, the composition is formulated in individual doses comprising from approximately $10^3$ to approximately $10^{12}$ pfu. Preferably, it is formulated for intravenous, intramuscular, subcutaneous or intratumoral administration.

In one embodiment, the composition is for use for treating or preventing diseases or pathological condition caused by a pathogenic organism or an unwanted cell division.

In still a further aspect, the invention provides a method of treatment and a method for inhibiting tumor cell growth comprising administering the composition of the invention to a subject in need thereof in an amount sufficient to treat or prevent a disease or a pathological condition caused by a pathogenic organism or an unwanted cell division.

In one embodiment, said cancer is selected from the group consisting of renal cancer, prostate cancer, breast cancer, colorectal cancer, lung cancer, liver cancer, gastric cancer, bile duct carcinoma, endometrial cancer, pancreatic cancer and ovarian cancer and a cancer that overexpresses MUC1.

In another embodiment, said method or use is carried out in conjunction with one or more other therapeutic agents selected from the group consisting of surgery, radiotherapy, chemotherapy, cryotherapy, hormonal therapy, toxin therapy, immunotherapy, cytokine therapy, targeted cancer therapy, gene therapy, photodynamic therapy and transplantation. In a further embodiment, said method or use is carried out according to a prime boost approach which comprises sequential administrations of a priming composition(s) and a boosting composition(s).

In a further aspect, the invention relates to a method for eliciting or stimulating and/or re-orienting an immune response comprising administering the composition of the invention to a subject in need thereof, in an amount sufficient to activate the subject's immunity.

In one embodiment, the method results in at least one the following properties (a) the secretion of high levels of IFN-alpha from PBMC; (b) the activation of monocyte-derived dendritic cells; (c) the induction of T cell proliferation (e.g. as indirectly reflected by highly granzyme B+ T cells); (d) a better cytokine/chemokine profile in MDSC; (e) activation of APC; (f) a M2 to M1 conversion of human macrophages; and/or (g) the induction of immunity through a TLR9-mediated pathway or others innate immunity-stimulating pathways.

DETAILED DESCRIPTION OF THE INVENTION

Definitions

Figure 1:
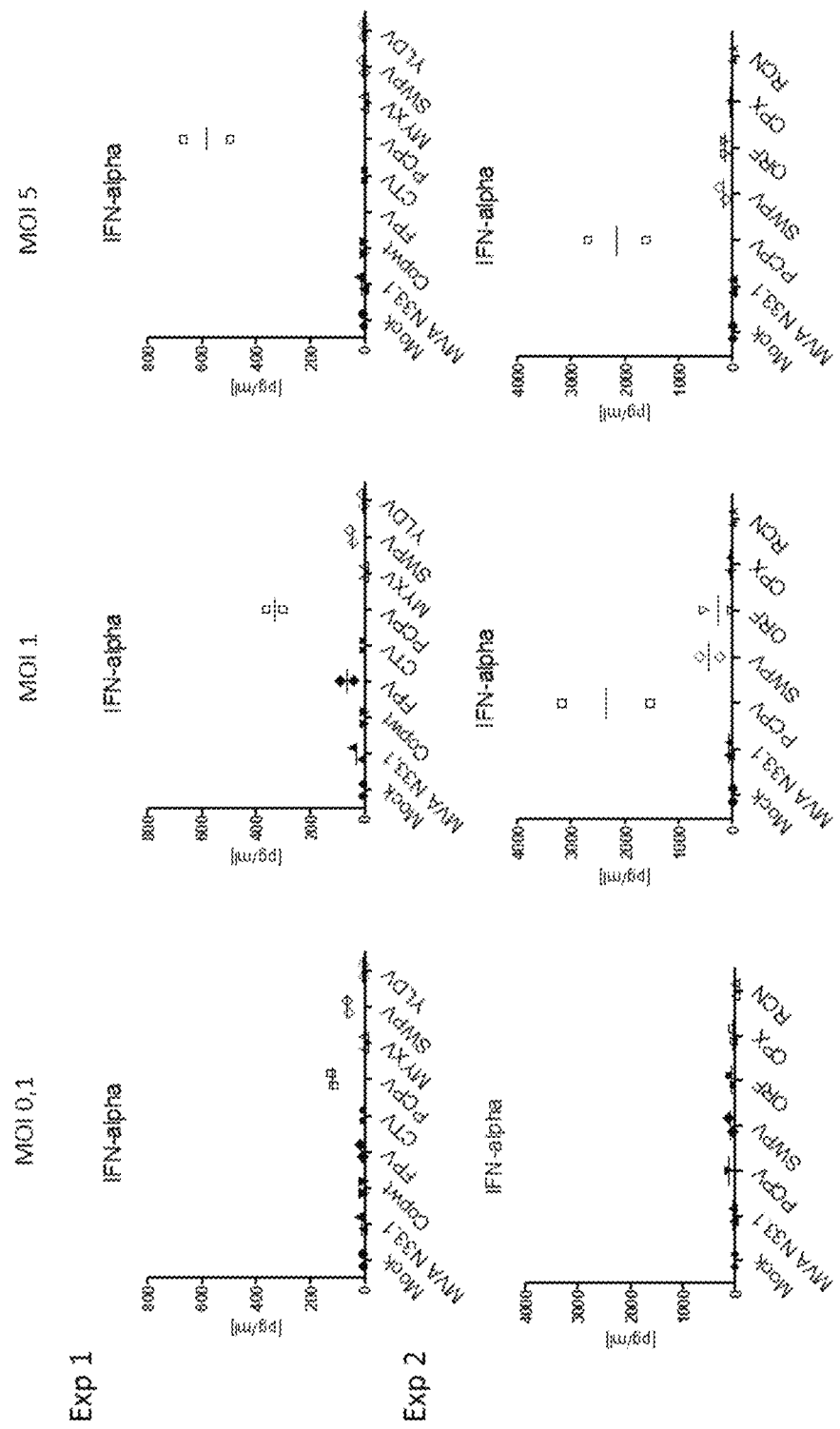
FIG. 1 illustrates IFN-alpha secretion in PBMCs from 2 donors in two different experiments (Exp 1 and exp 2) at different MOI (MOI 0.1; MOI 1 and MOI 5). Mock represents the negative control whereas the different viruses tested are Parapoxviruses (pseudocowpoxvirus (PCPV) and Parapoxvirus ovis (ORFV)), MVA (an empty MVA vector named MVAN33.1), cowpox virus (CPX), Copenhagen vaccinia virus (Copwt), fowlpox (FPV), Myxomavirus (MYXV), Swine pox (SWPV), raccoonpoxvirus (RCN), Cotiavirus (CTV) and Yaba-like disease virus (YLDV).

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "one or more" refers to either one or a number above one (e.g. 2, 3, 4, etc.).

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

As used herein, when used to define products and compositions, the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are open-ended and do not exclude additional, unrecited elements or method steps. The expression "consisting essentially of" means excluding other components or steps of any essential significance. Thus, a composition consisting essentially of the recited components would not exclude traces, contaminants and pharmaceutically acceptable carriers. "Consisting of" shall mean excluding more than trace elements of other components or steps.

The terms "polypeptide", "peptide" and "protein" refer to polymers of amino acid residues which comprise at least nine or more amino acids bonded via peptide bonds. The polymer can be linear, branched or cyclic and may comprise naturally occurring and/or amino acid analogues and it may be interrupted by non-amino acids. As a general indication, if the amino acid polymer is more than 50 amino acid residues, it is preferably referred to as a polypeptide or a protein whereas if it is 50 amino acids long or less, it is referred to as a "peptide".

Within the context of the present invention, the terms "nucleic acid", "nucleic acid molecule", "polynucleotide" and "nucleotide sequence" are used interchangeably and define a polymer of any length of either polydeoxyribonucleotides (DNA) (e.g. cDNA, genomic DNA, plasmids, vectors, viral genomes, isolated DNA, probes, primers and any mixture thereof) or polyribonucleotides (RNA) (e.g. mRNA, antisense RNA, SiRNA) or mixed polyribo-polydeoxyribonucleotides. They encompass single or double-stranded, linear or circular, natural or synthetic, modified or unmodified polynucleotides. Moreover, a polynucleotide may comprise non-naturally occurring nucleotides and may be interrupted by non-nucleotide components.

The terms "variant" "analog" "derivative" and the like can be used interchangeably to refer to a component (polypeptide, nucleic acid, virus, etc) exhibiting one or more modification(s) with respect to the native counterpart. Any modification(s) can be envisaged, including substitution, insertion and/or deletion of one or more nucleotide/amino acid residue(s). Preferred are variants that retain a degree of sequence identity of at least 75%, advantageously at least 80%, desirably at least 85%, preferably at least 90%, more preferably at least 95%, and even more preferably at least 98% identity after optimal global alignment with the sequence of the native counterpart, i.e. after alignment of the sequences to be compared taken in their entirety over their entire length. For illustrative purposes, "at least 75% identity" means 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. In a general manner, the term "identity" refers to an amino acid to amino acid or nucleotide to nucleotide correspondence between two polypeptides or nucleic acid sequences. The percentage of identity between two sequences is a function of the number of identical positions shared by the sequences, taking into account the number of gaps which need to be introduced for optimal alignment and the length of each gap. Various computer programs and mathematical algorithms are available in the art to determine the percentage of identity between amino acid sequences, such as for example the Blast program available at NCBI or ALIGN in Atlas of Protein Sequence and Structure (Dayhoffed, 1981, Suppl., 3: 482-9). Programs for determining identity between nucleotide sequences are also available in specialized data base (e.g. Genbank, the Wisconsin Sequence Analysis Package, BESTFIT, FASTA and GAP programs). For optimal global alignments, the algorithm of Needleman and Wunsch (Needleman and Wunsch. J. Mol. Biol. 48,443-453, 1970) may be used, for instance using the Emboss Needle software available at https://www.ebi.ac.uk/Tools/psa/emboss_needle/. This software reads two input sequences and writes their optimal global sequence alignment to file. It uses the Needleman-Wunsch alignment algorithm to find the optimum alignment (including gaps) of two sequences along their entire length. The algorithm uses a dynamic programming method to ensure the alignment is optimum, by exploring all possible alignments and choosing the best. A scoring matrix is read that contains values for every possible residue or nucleotide match. Needle finds the alignment with the maximum possible score where the score of an alignment is equal to the sum of the matches taken from the scoring matrix, minus penalties arising from opening and extending gaps in the aligned sequences. The substitution matrix and gap opening and extension penalties are user-specified. In the context of the invention, in order to obtain an optimal global alignment, the Emboss Needle software may be used with default parameters, i.e.:

For amino acid sequences: "Gap open"=10.0, "Gap extend"=0.5, "End gap penalty"="false", "End gap open"=10.0, "End gap extend"=0.5, and a "Blosum 62" matrix;

For nucleotide sequences: "Gap open"=10.0, "Gap extend"=0.5, "End gap penalty"="false", "End gap open"=10.0, "End gap extend"=0.5, and a "DNAfull" matrix.

As used herein, the term "host cell" should be understood broadly without any limitation concerning particular organization in tissue, organ, or isolated cells. Such cells may be of a unique type of cells or a group of different types of cells such as cultured cell lines, primary cells and dividing cells. In the context of the invention, the term "host cells" refers more particularly to eukaryotic cells and, notably, to mammalian (e.g. human or non-human) cells as well as to cells capable of producing the PCPV virus of the invention (e.g. producer cell). This term also includes cells which can be or has been the recipient of the virus described herein as well as progeny of such cells.

The terms "virus", 'viral particle", "viral vector" and virion" are used interchangeably and are to be understood broadly as meaning a vehicle comprising at least one element of a wild-type virus genome that may be packaged into a viral particle (also designated as a viral vector) or to the viral particle itself. Usually, a virus comprises a DNA or RNA viral genome packaged into a viral capsid and, in the case of an enveloped virus, lipids and other components (e.g. host cell membranes, etc). The present invention encompasses wild-type and engineered viruses. As mentioned just above, the term "virus" and the like has to be understood broadly as including viral vector (e.g. DNA viral vector) as well as viral particles generated thereof. The term "infectious" refers to the ability of a virus to infect and enter into a host cell or subject.

The term "naturally occurring" "native" or "wild type" is used to describe a biological molecule or organism that can be found in nature as distinct from being artificially produced by man. For example, a naturally occurring, native or wild-type virus refers to a virus which can be isolated from a source in nature or obtained from specific collections (e.g. ECCAC, ATCC, CNCM, etc). A biological molecule or an organism which has been intentionally modified by man in the laboratory is not naturally occurring. Representative examples of non-naturally occurring viruses include, among many others, recombinant viruses engineered by insertion of one or more nucleic acid(s) of interest in the viral genome and/or defective virus resulting from one or more modification(s) in the viral genome (e.g. total or partial deletion of a viral gene).

The term "obtained from", "originating" or "originate" is used to identify the original source of a component (e.g. a polypeptide, nucleic acid molecule, virus, etc) but is not meant to limit the method by which the component is made which can be, for example, by chemical synthesis, homologous recombination, recombinant means or any other means.

The term "treatment" (and any form of treatment such as "treating", "treat") as used herein encompasses prophylaxis (e.g. preventive measure in a subject at risk of having the pathological condition) and/or therapy (e.g. in a subject diagnosed as having the pathological condition), optionally in association with conventional therapeutic modalities. The result of the treatment is to slow down, cure, ameliorate or control the progression of the targeted pathological condition. For example, a subject is successfully treated for a cancer if after administration of a PCPV as described herein, alone or in combination, the subject shows an observable improvement of its clinical status.

The term "administering" (or any form of administration, such as "administered") as used herein refers to the delivery to a subject of a therapeutic agent such as the PCPV described herein.

The term "subject" generally refers to an organism for whom any product and method of the invention is needed or may be beneficial. Typically, the subject is a mammal, particularly a mammal selected from the group consisting of domestic animals, farm animals, sport animals, and primates. Preferably, the subject is a human who has been diagnosed as having or at risk of having a pathological disease (e.g. a cancer). The terms "subject" and "patients" may be used interchangeably when referring to a human organism and encompasses male and female. The subject to be treated may be a new-born, an infant, a young adult, an adult or an elderly.

Pseudocowpox Virus

In a first aspect, the present invention provides a pseudo-cowpoxvirus (PCPV) comprising at least one foreign nucleic acid inserted in its genome. In one embodiment said PCPV is for use for treating disease such as proliferative or infectious diseases as described hereinafter.

The term "pseudocowpox virus" or "PCPV" is used herein according to its plain ordinary meaning within Virology and refers to a member of the Poxviridae family which replicates in the cytoplasm of its host and belonging to the Parapoxvirus genus. PCPV possesses a linear and double-stranded DNA genome, typically of 130-150 kilobases. The present invention encompasses naturally occurring forms of pseudocowpox virus of any strain as well as variants thereof which may be modified for various purposes including those described herein.

The parapoxvirus genus encompasses a series of different species including Parapoxvirus ovis (ORFV), pseudocow-pox virus (PCPV) and bovine papular stomatitis virus (BPSV) and in each species different strains have been described in the art with disclosure of complete or partial genomic sequences; e.g. 01701, NZ2, NZ7, IA82, F07.821R, F09.1160S and SA00 strains of ORFV and AR02 and V660 strains of bovine papular stomatitis virus. Representative examples of suitable PCPV strains for use herein include, without limitation, YG2828 (Genbank accession number LC230119), F07.801R (Genbank accession number JF773693), F10.3081C (Genbank accession number JF773695), F07.798R (Genbank accession number JF773692), F99.177C (Genbank accession number AY453678), IT1303/05 (Genbank accession number JF800906), F00.120R (Genbank accession number GQ329669; Tikkanen et al., 2004, J. Gen. Virol. 85: 1413-8) and TJS (also called VR634; Genbank accession number GQ329670; Friedman-Kien et al., 1963, Science 140: 1335-6; available at ATCC under accession number VR634). Such strains may have morphological, structural and/or genetic differences each other, e.g., in terms of ITR length, number of predicted genes and/or G C rich content (see e.g. Hauta-niemi et al., 2010, J. Gen. Virol. 91: 1560-76).

In the context of the present invention, preference is given to the PCPV species. In a preferred embodiment, the PCPV virus of the present invention is obtained from the wild-type TJS strain as identified by ATCC reference number ATCC VR-634™ or from a virus strain of the same or similar name and functional fragments and variants thereof. Preferably, such a variant maintains at least 75% identity at the nucleotide or amino acid level with at least a segment of 10 kilobase (e.g. a continuous sequence of 10 kb) in the wild-type TJS pseudocowpox virus genome.

Exemplary modifications that are appropriate in the context of the present invention include without any limitation insertion(s), substitution(s) and/or deletion(s) of one or more nucleotide(s) within the PCPV genome with the goal of modulating (e.g. increase or decrease) expression of one or more viral gene or virus infectivity when compared to the wild-type pseudocowpox virus (e.g. TJS strain) or increasing its therapeutic efficacy (e.g. increase the ability of the PCPV virus to differentially express in diseased cells relative to healthy cells) or insertion of one or more foreign nucleic acid(s) of therapeutic interest or generating a chimeric virus containing PCPV genomic fragment(s) with ones obtained from a different virus origin.

In one and preferred embodiment, the PCPV of the invention comprises inserted in its genome at least one foreign nucleic acid (e.g. resulting in a recombinant PCPV virus). Alternatively, or in combination, the PCPV virus may be defective for a viral function encoded by the PCPV genome (e.g. a non-essential viral function), preferably for a viral gene function encoded at the insertion site(s) of the foreign nucleic acid.

Recombinant PCPV

The term "recombinant" as used herein in connection with the virus of the present invention indicates that the virus has been modified by the introduction of at least one foreign nucleic acid (also called recombinant gene or nucleic acid), notably a nucleic acid of therapeutic interest as described herein. In the context of the invention, the "foreign nucleic acid" that is inserted in the PCPV genome is not found in or expressed by a naturally-occurring PCPV genome. Nevertheless, the foreign nucleic acid can be homologous or heterologous to the subject into which the recombinant PCPV is introduced. More specifically, it can be of human origin or not (e.g. of bacterial, yeast or viral origin except PCPV). Advantageously, said foreign nucleic acid encodes a polypeptide or is a nucleic acid sequence capable of binding at least partially (by hybridization) to a complementary cellular nucleic acid (e.g., DNA, RNA, miRNA) present in a diseased cell with the aim of inhibiting a gene involved in said disease. A polypeptide is understood to be any translational product of a polynucleotide regardless of size, and whether glycosylated or not, and includes peptides and proteins. Such a foreign nucleic acid may be a native gene or portion(s) thereof (e.g. cDNA), or any variant thereof obtained by mutation, deletion, substitution and/or addition of one or more nucleotides.

In a preferred embodiment, the foreign nucleic acid encodes a polypeptide which is capable of providing a therapeutic or prophylactic activity when administered appropriately to a subject (i.e. a polypeptide of therapeutic interest), leading to a beneficial effect on the course or a symptom of the pathological condition to be treated. A vast number of polypeptides of therapeutic interest may be envisaged. In one embodiment, the foreign nucleic acid encodes a polypeptide selected from the group consisting of polypeptides that compensate for defective or deficient proteins in a subject, polypeptides that act through toxic effects to limit or remove diseased cells from the body (e.g. suicide gene products); polypeptides capable of potentiating anti-tumor efficacy (e.g. armed gene products); and polypeptides capable of inducing or activating an immune response (such as immunostimulatory and antigenic polypeptides). A foreign nucleic acid encoding a detectable gene product may also be useful in the context of the invention.

Immunostimulatory Polypeptides

As used herein, the term "immunostimulatory polypeptide" refers to a polypeptide which has the ability to stimulate the immune system, in a specific or non-specific way. A vast number of polypeptides are known in the art for their ability to exert an immunostimulatory effect. Examples of suitable immunostimulatory proteins in the context of the invention include without limitation cytokines, with a specific preference for interleukins (e.g. IL-2, IL-6, IL-12, IL-15, IL-24), chemokines (e.g. CXCL10, CXCL9, CXCL11), interferons (e.g. IFNα, IFNβ, IFNγ), tumor necrosis factor (TNF), colony-stimulating factors (e.g. GM-CSF, C-CSF, M-CSF . . . ), APC (for Antigen Presenting Cell)-exposed proteins (e.g. B7.1, B7.2 and the like), polypeptides having an anti-angiogenic effect (e.g. inhibitors of Vascular Endothelial Growth Factor such as bevacizumab or ranibizumab) and polypeptides that affect the regulation of cell surface receptors such as agonists or antagonists of immune checkpoints (e.g. antibodies directed to PD1 or its ligand (e.g. anti-PD-L1), CTLA4, LAG3, OX40 etc). In a preferred embodiment, the immunostimulatory polypeptide is an interleukin or a colony-stimulating factor (e.g. GM-CSF) or an agonist OX40-directed antibody.

Antigenic Polypeptides

As illustrated in the Example section, PCPV can stimulate innate (non-specific) immunity of the injected subject. Therefore, combining this effect with expression of an antigenic polypeptide may provide a virus capable of stimulating both innate and specific immune responses. This can be of importance for obtaining an effective anti-cancer response and for vaccination purposes for providing protection against a specific pathogen. Such effect may last for weeks.

The term "antigenic" refers to the ability to induce or stimulate a measurable immune response in a subject into which the recombinant PCPV encoding the polypeptide qualified as antigenic has been introduced. The stimulated or induced immune response against the antigenic polypeptide expressed by said recombinant PCPV can be humoral and/or cellular (e.g. production of antibodies, cytokines and/or chemokines involved in the activation of effector immune cells). The stimulated or induced immune response usually contributes in a protective effect in the administered subject. A vast variety of direct or indirect biological assays are available in the art to evaluate the antigenic nature of a polypeptide either in vivo (animal or human subjects), or in vitro (e.g. in a biological sample). For example, the ability of a particular antigen to stimulate innate immunity can be performed by for example measurement of the NK/NKT-cells (e.g. representativity and level of activation), as well as, IFN-related cytokine and/or chemokine producing cascades, activation of TLRs and other markers of innate immunity (Scott-Algara et al., 2010 PLOS One 5(1), e8761; Zhou et al., 2006, Blood 107, 2461-2469; Chan, 2008, Eur. J. Immunol. 38, 2964-2968). The ability of a particular antigen to stimulate a cell-mediated immune response can be performed for example by quantification of cytokine(s) produced by activated T cells including those derived from CD4+ and CD8+ T-cells using routine bioassays (e.g. characterization and/or quantification of T cells by ELISpot, by multiparameters flow cytometry, ICS, by cytokine profile analysis using multiplex technologies or ELISA), by determination of the proliferative capacity of T cells (e.g. T cell proliferation assays by [$^3$H] thymidine incorporation assay), by assaying cytotoxic capacity for antigen-specific T lymphocytes in a sensitized subject or by identifying lymphocyte subpopulations by flow cytometry and by immunization of appropriate animal models, as described herein.

It is contemplated that the term antigenic polypeptide encompasses native antigen as well as fragment (e.g. epitopes, immunogenic domains, etc) and variant thereof, provided that such fragment or variant is capable of being the target of an immune response. Preferred antigenic polypeptides for use herein are tumor-associated antigens and antigens of pathogenic organisms (bacteria, viruses, parasites, fungi, viroids or prions). It is within the scope of the skilled artisan to select the one or more antigenic polypeptide that is appropriate for treating a particular pathological condition.

In one embodiment, the antigenic polypeptide(s) encoded by the PCPV virus is/are cancer antigen(s) (also called tumor-associated antigens) that is associated with and/or serve as markers for cancers. Cancer antigens encompass various categories of polypeptides, e.g. those which are normally silent (i.e. not expressed) in healthy cells, those that are expressed only at low levels or at certain stages of differentiation and those that are temporally expressed such as embryonic and foetal antigens as well as those resulting from mutation of cellular genes, such as oncogenes (e.g. activated ras oncogene), proto-oncogenes (e.g. ErbB family), or proteins resulting from chromosomal translocations.

Some non-limiting examples of cancer antigens include, without limitation, MART-1/Melan-A, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family (e.g. MUC1, MUC16, etc; see e.g. U.S. Pat. No. 6,054,438; WO98/04727; or WO98/37095), HER2/neu, p21ras, RCAS1, alpha-fetoprotein, E-cadherin, alpha-catenin, beta-catenin and gamma-catenin, p120ctn, gp100.sup.Pmel117, PRAME, NY-ESO-1, cdc27, adenomatous polyposis coli protein (APC), fodrin, Connexin 37, Ig-idiotype, p15, gp75, GM2 and GD2 gangliosides, Smad family of cancer antigens brain glycogen phosphorylase, SSX-1, SSX-2 (HOM-MEL-40), SSX-1, SSX-4, SSX-5, SCP-1 and CT-7, and c-erbB-2.

The cancer antigens may also encompass antigens encoded by pathogenic organisms that are capable of inducing a malignant condition in a subject (especially chronically infected subject) such as RNA and DNA tumor viruses (e.g. HPV, HCV, HBV, EBV, etc) and bacteria (e.g. *Helicobacter pilori*).

Viral antigenic polypeptides for use in this invention include for example antigens from hepatitis virus A, B, C, D or E, immunodeficiency virus (e.g. HIV), herpes viruses (HSV), cytomegalovirus, varicella zoster, papilloma virus (HPV), Epstein Barr virus (EBV), influenza virus, parainfluenza virus, adenovirus, coxsakie virus, picorna virus, rotavirus, respiratory syncytial virus, poxvirus, rhinovirus, rubella virus, papovirus, mumps virus, measles virus. Some non-limiting examples of HIV antigens include gp120 gp40, gp160, p24, gag, pol, env, vif, vpr, vpu, tat, rev, nef tat, nef. Some non-limiting examples of human herpes virus antigens include gH, gL gM gB gC gK gE or gD or Immediate Early protein such as ICP27, ICP47, ICP4, ICP36 from HSV1 or HSV2. Some non-limiting examples of cytomegalovirus antigens include gB. Some non-limiting examples of derived from Epstein Barr virus (EBV) include gp350 and the EBV-encoded nuclear antigen (EBNA)-1. Some non-limiting examples of Varicella Zoster Virus antigens include gp1, 11, 111 and 1E63. Some non-limiting examples of hepatitis C virus (HCV) antigens includes E1 or E2 env protein, core protein, NS2, NS3, NS4a, NS4b, NS5a and NS5b. Some non-limiting examples of hepatitis B virus (HBV) antigens includes polymerase, core and env polypeptide (e.g., the combination of HBV antigens described in WO2013/007772). Some non-limiting examples of human papilloma virus (HPV) antigens include L1, L2, E1, E2, E3, E4, E5, E6, E7. Antigens derived from other viral pathogens, such as Respiratory Syncytial virus (e.g. F and G proteins), parainfluenza virus, measles virus, mumps virus, flaviviruses (e.g. Yellow Fever Virus, Dengue Virus, Tick-borne encephalitis virus, Japanese Encephalitis Virus) and Influenza virus cells (e.g. HA, NP, NA, or M proteins) can also be used in accordance with the present invention. In a preferred embodiment, the PCPV of the invention is engineered to encode and express HPV-16 or HPV-18 E6 and/or E7 antigens.

Bacterial antigenic polypeptides include for example antigens from Mycobacteria causing TB and leprosy, pneumocci, aerobic gram negative bacilli, mycoplasma, staphyloccocus, streptococcus, salmonellae, chlamydiae, neisseriae and the like.

Parasitic antigenic polypeptides include for example antigens from malaria, leishmaniasis, trypanosomiasis, toxoplasmosis, schistosomiasis and filariasis.

Preferred antigenic polypeptides for expression by the PCPV of the present invention are
 the MUC-1 antigen aberrantly glycosylated and overexpressed in a variety of epithelial cancers;
 the HPV-16 E7 antigen, in particular a non-oncogenic variant thereof.
 HBV antigens, in particular a fusion comprising HBV polymerase, HBV core protein and HBsAg immunogenic domains (e.g. as described in WO2013/007772)

Suicide Gene Products

The term "suicide gene product" refers to a polypeptide able to convert a precursor of a drug, also named "prodrug", into a cytotoxic compound. Examples of suicide gene products and corresponding prodrugs are disclosed in the following table:

TABLE 1

| Suicide gene product | Prodrug |
| --- | --- |
| Thymidine Kinase | Ganciclovir; Ganciclovir elaidic acid ester; penciclovir; Acyclovir; Valacyclovir; (E)-5-(2-bromovinyl)-2'-deoxyuridine; zidovudine; 2'-Exo-methanocarbathymidine |
| Cytosine deaminase | 5-Fluorocytosine |
| Purine nucleoside phosphorylase | 6-Methylpurine deoxyriboside; Fludarabine |
| Uracil phosphoribosyl transferase | 5-Fluorocytosine; 5-Fluorouracil |
| Thymidylate kinase | Azidothymidine |

Desirably, the PCPV of the invention carries in its genome a suicide gene encoding a polypeptide having at least cytosine deaminase (CDase) activity. In the prokaryotes and lower eukaryotes (it is not present in mammals), CDase is involved in the pyrimidine metabolic pathway by which exogenous cytosine is transformed into uracil by means of a hydrolytic deamination. CDase also deaminates an analogue of cytosine, i.e. 5-fluorocytosine (5-FC), thereby forming 5-fluorouracil (5-FU), a compound which is cytotoxic by itself but even more when it is converted into 5-fluoro-UMP (5-FUMP) by the action of uracil phosphoribosyl transferase (UPRTase).

CDase and UPRTase encoding nucleic acid can be obtained from any prokaryotes and lower eukaryotes. Gene sequences and encoded enzymes have been published and are available in specialized data banks such as SWISSPROT EMBL, Genbank, Medline and the like). *Saccharomyces cerevisiae* CDase (FCY1 gene) and/or UPRTase (FUR1 gene) are preferred in the context of this invention (Kern et al., 1990, Gene, 88: 149-57). Functional variants of these genes may also be used. Such variants preferably retain a degree of identity of at least 75%, with the amino acid sequence of the native counterpart. A N-terminally truncated UPRTase functional analogue is particularly useful in the context of the invention due to its ability to exhibit a higher UPRTase activity than that of the native enzyme (e.g. as described in EP998568 with a deletion of the 35 first residues up to the second Met residue of the native protein). Also preferred is a polypeptide having both CDase and UPRTase activities engineered by fusion of two enzymatic activities (see e.g. FCY1::FUR1 and FCY1::FUR1[Delta] 105 (FCU1) and FCU1-8 polypeptides described in WO96/16183, EP998568 and WO2005/07857). Of particular interest is the FCU1 suicide gene (or FCY1::FUR1[Delta] 105 fusion) encoding a polypeptide comprising the amino acid sequence represented in the sequence identifier SEQ ID NO: 1 of WO2009/065546).

Armament Gene Products

Other foreign nucleic acids may be used in the context of the invention to arm the PCPV virus with the aim of potentiating anti-tumor efficacy. In one embodiment, the armed gene product is selected from the group consisting of nucleoside pool modulators (e.g., cytidine deaminase and notably yeast cytidine deaminase (CDD1) or human cytidine deaminase (hCD); see EP16306831.5); polypeptides acting on metabolic and immune pathways (e.g., adenosine deaminase and notably the human adenosine deaminase huADA1 or huADA2; see EP17306012.0); polypeptides acting on the apoptotic pathway; endonucleases (like restriction enzymes, CRISPR/Cas9), and target-specific RNAs (e.g., miRNA, shRNA, siRNA).

Detectable Gene Products

Typically, such a polypeptide is detectable by spectroscopic, photochemical, biochemical, immunochemical, chemical, or other physical means and thus may permit to identify the recombinant PCPV within a host cell or subject. Non-limiting examples of suitable detectable gene products includes mCherry, Emerald, firefly luciferase and green fluorescent proteins (GFP and enhanced version thereof e-GFP) detectable by fluorescent means as well as beta-galactosidase detectable by colorimetric means.

The present invention also encompasses PCPV expressing two or more polypeptides of interest as described herein, e.g. at least two antigenic polypeptides (e.g. HPV-16 E6 and E7 polypeptides), at least one antigen and one cytokine (e.g. MUC1 antigen and IL-2), at least two antigens and one cytokine (e.g. HPV E6 and E7 antigens and IL-2), etc.

In the context of the present invention, the encoded polypeptide of interest for use herein may incorporate structural features which are beneficial to its expression by the PCPV of the invention and its therapeutic effect in the subject; such as ones permitting to facilitate cloning in the PCPV genome (modification of potential cleavage sites), to reinforce antigenic nature (modification of glycosylation sites) and/or to improve MHC class I and/or MHC class II presentation (e.g. membrane anchorage). Membrane anchorage can be achieved by incorporating in the polypeptide of interest a membrane-anchoring sequence and a secretory sequence (i.e. a signal peptide) if the native polypeptide lacks it. Briefly, signal peptides usually comprise 15 to 35 essentially hydrophobic amino acids which are then removed by a specific ER (endoplasmic reticulum)-located endopeptidase to give the mature polypeptide. Trans-membrane peptides are also highly hydrophobic in nature and serve to anchor the polypeptides within cell membrane. The choice of the trans-membrane and/or signal peptides which can be used in the context of the present invention is vast. They may be obtained from cellular or viral polypeptides such as those of immunoglobulins, tissue plasminogen activator, insulin, rabies glycoprotein, the HIV virus envelope glycoprotein or the measles virus F protein or may be synthetic. Preferably, the secretory sequence is inserted at the N-terminus of the polypeptide downstream of the codon for initiation of translation and the membrane-anchoring sequence at the C-terminus, preferably immediately upstream of the stop codon.

Generation and Expression of the Foreign Nucleic Acid(s)

The foreign nucleic acid(s) to be expressed by the PCPV of the present invention may be easily generated by a number of ways known to those skilled in the art (e.g. cloning, PCR amplification, DNA shuffling). For example, such a foreign nucleic acid can be isolated from any available source (e.g. biologic materials described in the art, cDNA and genomic libraries, or any prior art vector known to include it) using sequence data available to the skilled person (e.g. publications, patent applications, Genbank, etc.) and then suitably inserted in the PCPV genome. Alternatively, they can also be generated by chemical synthesis in automatized process (e.g. assembled from overlapping synthetic oligonucleotides or synthetic gene). Preferably, such a foreign nucleic acid is obtained from cDNA and does not comprise intronic sequences. Modification(s) can be generated by a number of ways known to those skilled in the art, such as chemical synthesis, site-directed mutagenesis, PCR mutagenesis, etc.

In the context of the present invention, the foreign nucleic acid can be optimized for providing high level expression in a particular host cell or subject. It has been indeed observed that, the codon usage patterns of organisms are highly non-random and the use of codons may be markedly different between different hosts. As the foreign nucleic acid might be from prokaryote (e.g. bacterial or viral antigen) or lower eukaryote origin (e.g. suicide gene product), it may have an inappropriate codon usage pattern for efficient expression in higher eukaryotic cells (e.g. human). Typically, codon optimization is performed by replacing one or more "native" codon corresponding to a codon infrequently used by one or more codon encoding the same amino acid which is more frequently used in the subject to treat. It is not necessary to replace all native codons corresponding to infrequently used codons since increased expression can be achieved even with partial replacement.

Further to optimization of the codon usage, expression can also be improved through additional modifications of the foreign nucleic acid. For example, the nucleic acid sequence can be modified so as to prevent clustering of rare, non-optimal codons being present in concentrated areas and/or to suppress or modify "negative" sequence elements which are expected to negatively influence expression levels. Such negative sequence elements include without limitation the regions having very high (>80%) or very low (<30%) GC content; AT-rich or GC-rich sequence stretches; unstable direct or inverted repeat sequences; R A secondary structures; and/or internal cryptic regulatory elements such as internal TATA-boxes, chi-sites, ribosome entry sites, and/or splicing donor/acceptor sites.

Moreover, when homologous foreign nucleic acids need to be expressed by the PCPV of the invention, at least one of the homologous sequences (at least portion thereof) can be degenerated over the full-length nucleic acid or portion(s) thereof so as to reduce sequence identity. It is indeed advisable to degenerate the portions of sequences that show a high degree (e.g. at least 70%) of sequence identity so as to avoid homologous recombination problems during production process and the skilled person is capable of identifying such portions by sequence alignment. Examples of proper sequence degeneration applied to HPV antigens obtained from various serotypes (e.g. HPV-16 and HPV-18 E6 and/or E7 antigens) can be found in WO2008/092854.

In one embodiment, the foreign nucleic acid(s) to be inserted in and expressed by the PCPV of the invention is/are operably linked to suitable regulatory elements for expression in a desired host cell or subject.

As used herein, the term "regulatory elements" or "regulatory sequence" refers to any element that allows, contributes or modulates the expression of the nucleic acid(s) in a given host cell or subject, including replication, duplication, transcription, splicing, translation, stability and/or transport of the nucleic acid(s) or its derivative (i.e. m RNA). As used herein, "operably linked" means that the elements being linked are arranged so that they function in concert for their intended purposes. For example, a promoter is operably linked to a nucleic acid if the promoter effects transcription from the transcription initiation to the terminator of said nucleic acid at least in a permissive host cell.

It will be appreciated by those skilled in the art that the choice of the regulatory sequences can depend on factors such as the nucleic acid(s) itself, the level of expression desired, etc. The promoter is of special importance. In the context of the invention, it can be constitutive directing expression of the foreign nucleic acid in many types of cells or specific to certain types of cells or tissues or regulated according to the phase of a viral cycle (e.g. late, intermediate or early). One may also use promoters that are repressed during the production step in response to specific events or exogenous factors (e.g. specific components, temperature, etc), in order to optimize production of the recombinant PCPV and circumvent potential toxicity of the expressed polypeptide(s).

Poxvirus promoters are particularly adapted for expression in recombinant PCPV. In one embodiment, the foreign nucleic acid inserted in the PCPV genome is placed under the control of a poxvirus promoter, preferably, a vaccinia virus promoter and more preferably one selected from the group consisting of the 7.5K, H5R, 11K7.5 (Erbs et al., 2008, Cancer Gene Ther. 15(1): 18-28), SE, TK, pB2R, p28, p11 and K1L promoter, synthetic promoters such as those described in Chakrabarti et al. (1997, Biotechniques 23: 1094-7; Hammond et al, 1997, J. Virol Methods 66: 135-8; and Kumar and Boyle, 1990, Virology 179: 151-8) and early/late chimeric promoters.

Those skilled in the art will appreciate that the regulatory elements controlling the expression of the at least one foreign nucleic acid may further comprise additional elements for proper initiation, regulation and/or termination of transcription (e.g. polyA transcription termination sequences), mRNA transport (e.g. nuclear localization sequences), translation (e.g. an initiator Met, tripartite leader sequences, etc.), processing (e.g. signal peptides, transmembrane anchorage sequences, etc) and purification steps (e.g. a tag).

Insertion within the PCPV Genome and Generation of the Recombinant PCPV

Insertion of the at least one foreign nucleic acid(s) (equipped with appropriate regulatory elements) in the PCPV genome is made by conventional means, either using appropriate restriction enzymes or, preferably by homologous recombination.

In another aspect, the present invention provides a method for generating the recombinant PCPV of the invention by homologous recombination between a transfer plasmid comprising the foreign nucleic acid (with its regulatory elements) flanked in 5' and 3' with PCPV sequences respectively present upstream and downstream the insertion site and a PCPV genome. In one embodiment, said method comprise a step of generating said transfer plasmid (e.g. by conventional molecular biology methods) and a step of introducing said transfer plasmid into a suitable host cell, notably together with a PCPV virus comprising the flanking sequence present in the transfer plasmid (e.g. a wild-type PCPV virus). Preferably, the transfer plasmid is introduced into the host cell by transfection and the PCPV virus by infection.

The size of each flanking PCPV sequence may vary. It is usually at least 100 bp and at most 1500 bp, with a preference for approximately 150 to 500 bp on each side of the foreign nucleic acid, advantageously from 180 to 450 bp, preferably from 200 to 400 bp and more preferably from 250 to 350 bp with a specific preference for approximately 300 bp on each side of the foreign nucleic acid to be inserted.

Various sites of insertion may be considered in the PCPV genome including, without any limitation, in a viral gene, with a preference for a non-essential viral gene, in an intergenic region, in a portion of the PCPV genome which does not encode gene products or in duplicated locus (genes or locus which occur in 2 or more copies in the native virus genome). Upon insertion of the foreign nucleic acid(s) into the PCPV genome according to the method of the invention, the viral locus at the insertion site may be deleted at least partially. In one embodiment, this deletion or partial deletion may result in suppressed expression of the viral gene product encoded by the deleted PCPV sequence resulting in a defective PCPV virus for said virus function.

Examples of insertion sites are given in U.S. Pat. No. 6,365,393. In a preferred embodiment, the foreign nucleic acid(s) is/are inserted in a non-essential and duplicated locus of the PCPV genome with a preference for the VEGF locus (Rziha et al., 2000, J. Biotechnol. 83(1-2): 137-145). It has to be noted that VEGF gene exists in 2 copies in the PCPV genome and the present invention contemplates either insertion in both VEGF locus or in only one (leaving a copy intact for providing viral function). Preferably, the foreign nucleic acid is inserted in both VEGF locus resulting in two copies of the foreign nucleic acid inserted in the PCPV genome.

In certain embodiments, the method of the present invention further uses a selection and/or a detectable gene to facilitate identification of the recombinant PCPV. In preferred embodiments, the transfer plasmid further comprises a selection marker with a specific preference for the GPT gene (encoding a guanine phosphoribosyl transferase) permitting growth in a selective medium (e.g. in the presence of mycophenolic acid, xanthine and hypoxanthine) or a detectable gene encoding a detectable gene product such as GFP, e-GFP or mCherry. In one embodiment, the transfer plasmid is introduced into the host cell in the presence of an endonuclease capable of providing a double-stranded break in said selection or detectable gene. Said endonuclease may be in the form of a protein or expressed by an expression vector. Representative embodiments are illustrated in the Example section.

Homologous recombination permitting to generate the recombinant PCPV is preferably carried out in appropriate host cells (e.g. Bovine Turbinate cells).

Particularly preferred embodiments are methods for the generation of:

- a PCPV virus comprising inserted within one or both VEGF locus a nucleic acid encoding the human MUC-1 antigen (e.g. as described in WO92/07000 and U.S. Pat. No. 5,861,381) preferably under the transcriptional control of the early/late vaccinia pH5R promoter; or
- a PCPV virus comprising inserted within one or both VEGF locus a nucleic acid encoding a membrane anchored HPV-16 non-oncogenic E7 antigen (as described in WO99/03885) preferably under the transcriptional control of the early/late vaccinia p7.5 promoter.

Production of PCPV Virus

In another aspect, the present invention relates to a method for amplifying the PCPV of the invention. Preferably said method comprises the steps of a) preparing a producer cell line, b) transfecting or infecting the prepared producer cell line, c) culturing the transfected or infected producer cell line under suitable conditions so as to allow the production of the virus (e.g. infectious viral particles), d) recovering the produced virus from the culture of said producer cell line and optionally e) purifying said recovered virus.

In one embodiment, the producer cell is a mammalian (e.g. human or non-human) cell and preferably HeLa cells (e.g. ATCC-CRM-CCL-2™ or ATCC-CCL-2.2™).

Producer cells are preferably cultured in an appropriate medium which can, if needed, be supplemented with serum and/or suitable growth factor(s) or not (e.g. a chemically defined medium preferably free from animal- or human-derived products). An appropriate medium may be easily selected by those skilled in the art depending on the producer cells. Such media are commercially available. Producer cells are preferably cultivated at a temperature comprised between +30° C. and +38° C. (more preferably at approximately 37° C.) for between 1 and 8 days before infection. If needed, several passages of 1 to 8 days may be made in order to increase the total number of cells.

In step b), producer cells are infected by the PCPV virus described herein under appropriate conditions using an appropriate multiplicity of infection (MOI) to permit productive infection of producer cells. For illustrative purposes, an appropriate MOI ranges from $10^{-3}$ to 50, with a specific preference for a MOI comprises from 0.01 to 5. Infection step is carried out in a medium which may be the same as or different from the medium used for the culture of producer cells.

In step c), infected producer cells are then cultured under appropriate conditions well known to those skilled in the art until progeny virus (e.g. infectious virus particles) is produced. Culture of infected producer cells is also preferably performed in a medium which may be the same as or different from the medium/media used for culture of producer cells and for infection step, at a temperature between +32° C. and +37° C., for 1 to 5 days.

In step d), the virus produced in step c) is collected from the culture supernatant and/or the producer cells. Recovery from producer cells may require a step allowing the disruption of the producer cell membrane to allow the liberation of the virus. The disruption of the producer cell membrane can be induced by various techniques well known to those skilled in the art, including but not limited to: freeze/thaw, hypotonic lysis, sonication, microfluidization, high shear (also called high speed) homogenization or high-pressure homogenization.

Viral vectors may then be further purified, using purification steps well known in the art. Various purification steps can be envisaged, including clarification, enzymatic treatment (e.g. endonuclease, protease, etc), chromatographic and filtration steps. Appropriate methods are described in the art (e.g. in WO2007/147528).

Pharmaceutical Composition

In an aspect is provided a composition comprising a therapeutically effective amount of the PCPV described herein and a pharmaceutically acceptable vehicle. In embodiments, the PCPV is recombinant and comprises inserted in its genome one or more foreign nucleic acid (with suitable regulatory elements as described before), notably one or more foreign nucleic acid encoding an antigenic polypeptide such as a cancer antigen, an antigen originating from a pathogenic organism, and/or an immunostimulatory polypeptide, etc). In specific embodiment, the composition can comprise exosomes generated after PCPV infection.

A "therapeutically effective amount" corresponds to the amount of PCPV that is sufficient for producing beneficial results. Such a therapeutically effective amount may vary as a function of various parameters such as the mode of administration; the age and weight of the subject; the nature and extent of symptoms; the ability of the subject to respond to the treatment, kind of concurrent treatment; the frequency of treatment and/or the need for prevention or therapy, etc.

When "prophylactic" use is concerned, the composition is administered at a dose sufficient to prevent or to delay the onset and/or establishment and/or relapse of the pathological condition, especially in a subject at risk. For "therapeutic" use, the composition is administered to a subject diagnosed as having a disease or pathological condition with the goal of treating it, optionally in association with one or more conventional therapeutic modalities.

The term "pharmaceutically acceptable vehicle" is intended to include any and all carriers, solvents, diluents, excipients, adjuvants, dispersion media, coatings, antibacterial and antifungal agents, absorption agents and the like compatible with administration in mammals and in particular human subjects. Non-limiting examples of pharmaceutically acceptable vehicles include water, NaCl, normal saline solutions, lactated Ringers, saccharide solution (e.g. glucose, trehalose, saccharose, dextrose, etc) alcohols, oils, gelatins, carbohydrates such as lactose, amylose or starch, fatty acid esters, hydroxymethycellulose, and the like as well as other aqueous physiologically balanced salt solutions may be used (see for example the most current edition of Remington: The Science and Practice of Pharmacy, A. Gennaro, Lippincott, Williams&Wilkins).

In one embodiment, the PCPV composition of the invention is formulated appropriately to ensure its stability under the conditions of manufacture and long-term storage (i.e. for at least 6 months, with a preference for at least two years) at freezing (e.g. −70° C., −20° C.), refrigerated (e.g. 4° C.) or ambient (e.g. 20-25° C.) temperature. Such formulations generally include a liquid carrier such as aqueous solutions.

Advantageously, the formulation for use herein is suitably buffered for human use, preferably at physiological or slightly basic pH (e.g. from approximately pH 7 to approximately pH 9 with a specific preference for a pH comprised between 7 and 8 and more particularly close to 7.5). Suitable buffers include without limitation TRIS (tris(hydroxymethyl)methylamine), TRIS-HCl (tris(hydroxymethyl)methylamine-HCl), HEPES (4-2-hydroxyethyl-1-piperazineethanesulfonic acid), phosphate buffer (e.g. PBS), ACES (N-(2-Acetamido)-aminoethanesulfonic acid), PIPES (Piperazine-N,N'-bis(2-ethanesulfonic acid)), MOPSO (3-(N-Morpholino)-2-hydroxypropanesulfonic acid), MOPS (3-(N-morpholino)propanesulfonic acid), TES (2-{[tris(hydroxymethyl)methyl]amino}ethanesulfonic acid), DIPSO (3-[bis(2-hydroxyethyl)amino]-2-hydroxypropane-1-sulfonic acid), MOBS (4-(N-morpholino)butanesulfonic acid), TAPSO (3-[N-Tris(hydroxymethyl)methylamino]-2-hydroxypropanesulfonic Acid), HEPPSO (4-(2-Hydroxyethyl)-piperazine-1-(2-hydroxy)-propanesulfonic acid), POPSO (2-hydroxy-3-[4-(2-hydroxy-3-sulfopropyl)piperazin-1-yl]propane-1-sulfonic acid), TEA (triethanolamine), EPPS (N-(2-Hydroxyethyl)-piperazine-N'-3-propanesulfonic acid), and TRICINE (N-[Tris(hydroxymethyl)-methyl]-glycine). Preferably, said buffer is selected from TRIS-HCl, TRIS, Tricine, HEPES and phosphate buffer comprising a mixture of $Na_2HPO_4$ and $KH_2PO_4$ or a mixture of $Na_2HPO_4$ and $NaH_2PO_4$. Said buffer (in particular those mentioned above and notably TRIS-HCl) is preferably present in a concentration of 10 to 50 mM. It might be beneficial to also include in such formulations a monovalent salt so as to ensure an appropriate osmotic pressure. Said monovalent salt may notably be selected from NaCl and KCl, preferably said monovalent salt is NaCl, preferably in a concentration of 10 to 500 mM.

The formulation may also include a cryoprotectant so as to protect the virus-based composition at low storage temperature. Suitable cryoprotectants include without limitation sucrose (or saccharose), trehalose, maltose, lactose, mannitol, sorbitol and glycerol, preferably in a concentration of 0.5 to 20% (weight in g/volume in L, referred to as w/v). For example, sucrose is preferably present in a concentration of 5 to 15% (w/v).

The PCPV composition, and especially a liquid composition thereof, may further comprise a pharmaceutically acceptable chelating agent, and in particular an agent chelating dications for improving stability. The pharmaceutically acceptable chelating agent may notably be selected from ethylenediaminetetraacetic acid (EDTA), 1,2-bis(o-aminophenoxy)ethane-N,N,N',N'-tetraacetic acid (BAPTA), ethylene glycol tetraacetic acid (EGTA), dimercaptosuccinic acid (DMSA), diethylene triamine pentaacetic acid (DTPA), and 2,3-Dimercapto-1-propanesulfonic acid (DMPS). The pharmaceutically acceptable chelating agent is preferably present in a concentration of at least 50 μM with a specific preference for a concentration of 50 to 1000 μM. Preferably, said pharmaceutically acceptable chelating agent is EDTA present in a concentration close to 150 μM.

Additional compounds may further be present to increase stability of the PCPV composition. Such additional compounds include, without limitation, $C_2$-$C_3$ alcohol (desirably in a concentration of 0.05 to 5% (volume/volume or v/v)), sodium glutamate (desirably in a concentration lower than 10 mM), non-ionic surfactant (U.S. Pat. No. 7,456,009, US2007-0161085) such as Tween 80 (also known as polysorbate 80) at low concentration below 0.1%. Divalent salts such as $MgCl_2$ or $CaCl_2$ have been found to induce stabilization of various biological products in the liquid state (see Evans et al. 2004, J Pharm Sci. 93:2458-75 and U.S. Pat. No. 7,456,009). Amino acids, and in particular histidine, arginine or methionine, have been found to induce stabilization of various viruses in the liquid state (see WO2016/087457).

The presence of high molecular weight polymers such as dextran or polyvinylpyrrolidone (PVP) is particularly suited for freeze-dried compositions, usually obtained by a process involving vacuum drying and freeze-drying and the presence of these polymers assists in the formation of the cake during freeze-drying (see e.g. WO03/053463; WO2006/085082; WO2007/056847; WO2008/114021 and WO2014/053571).

In accordance with the present invention, formulation of the PCPV composition can also be adapted to the mode of administration to ensure proper distribution or delayed release in vivo. Biodegradable, biocompatible polymers can be used, such as ethylene vinyl acetate, polyanhydrides, polyglycolic acid, collagen, polyorthoesters, polylactic acid and polyethylene glycol. (see e.g. J. R. Robinson in "Sustained and Controlled Release Drug Delivery Systems", ed., Marcel Dekker, Inc., New York, 1978; WO01/23001; WO2006/93924; WO2009/53937).

For illustrative purposes, Tris-buffered formulations (Tris-HCl pH8) comprising saccharose 5% (w/v), sodium glutamate 10 mM, and NaCl 50 mM are adapted to the preservation of the composition of the invention from −20° C. to 5° C.

Dosage

The composition of the present invention can be formulated in individual doses, each dose containing from about $10^3$ to $10^{12}$ vp (viral particles), iu (infectious unit) or pfu (plaque-forming units) of a defined PCPV depending on the quantitative technique used. The quantity of a defined PCPV present in a sample can be determined by routine titration techniques, e.g. by counting the number of plaques following infection of permissive cells (e.g. HeLa cells) to obtain a plaque forming units (pfu) titer, by measuring the A260 absorbance (vp titers), or still by quantitative immunofluorescence, e.g. using anti-virus antibodies (iu titers). Further refinement of the calculations necessary to adapt the appropriate dosage for a subject or a group of subjects may be routinely made by a practitioner, in the light of the relevant circumstances. As a general guidance, individual doses which are suitable for PCPV composition comprise from approximately $10^3$ to approximately $10^{12}$ pfu, advantageously from approximately $10^4$ pfu to approximately $10^{11}$ pfu, preferably from approximately $10^5$ pfu to approximately $10^{10}$ pfu; and more preferably from approximately $10^6$ pfu to approximately $10^9$ pfu and notably individual doses of approximately $10^7$, $5\times10^7$, $10^8$ or $5\times10^8$ pfu are particularly preferred.

Administration

Any of the conventional administration routes is applicable in the context of the invention including parenteral, topical or mucosal routes. Parenteral routes are intended for administration as an injection or infusion and encompass systemic as well as local routes. Parenteral injection types that may be used to administer the PCPV composition include intravenous (into a vein, such as the portal vein feeding liver), intravascular (into a blood vessel), intraarterial (into an artery such as hepatic artery), intradermal (into the dermis), subcutaneous (under the skin), intramuscular (into muscle), intraperitoneal (into the peritoneum) and intratumoral (into a tumor or its close vicinity) and also scarification. Administration can be in the form of a single bolus dose, or may be, for example, by a continuous perfusion pump. Mucosal administrations include without limitation oral/alimentary, intranasal, intratracheal, intrapulmonary, intravaginal or intra-rectal route. Topical administration can also be performed using transdermal means (e.g. patch and the like). Preferably, the PCPV composition is formulated for intravenous, intramuscular, subcutaneous or intratumoral administration.

Administrations may use conventional syringes and needles (e.g. Quadrafuse injection needles) or any compound or device available in the art capable of facilitating or improving delivery of a virus in the subject (e.g. electroporation for facilitating intramuscular administration). An alternative is the use of a needleless injection device (e.g. Biojector™ device). Transdermal patches may also be envisaged.

The composition of the invention is suitable for a single administration or a series of administrations. It is also possible to proceed via sequential cycles of administrations that are repeated after a rest period. Intervals between each administration can be from three days to six months (e.g. 24 h, 48 h, 72 h, weekly, every two weeks, monthly or quarterly, etc). Intervals can also be irregular. The doses can vary for each administration within the range described above.

Therapeutic Use of the PCPV Composition and Method of Treatment

In another aspect, the invention relates to a recombinant pseudocowpoxvirus (PCPV) or a composition of the invention (in particular a pharmaceutical composition), for use as a medicament, in particular for treating or preventing diseases or pathological condition caused by a pathogenic organism or an unwanted cell division according to the modalities described herein, as well as to a method of treatment comprising administering the recombinant pseudocowpoxvirus (PCPV) or the composition of the invention to a subject in need thereof in an amount sufficient to treat or prevent such a disease or pathological condition. The invention also relates to the use of the recombinant pseudocowpoxvirus (PCPV) or the composition of the invention for the manufacture of a drug for treating or preventing diseases or pathological condition caused by a pathogenic organism or an unwanted cell division according to the modalities described herein. The invention also relates to the use of the recombinant pseudocowpoxvirus (PCPV) or the composition of the invention for treating or preventing diseases or pathological condition caused by a pathogenic organism or an unwanted cell division according to the modalities described herein. A preferred therapeutic scheme or treatment method involves 2 to 6 weekly administrations possibly followed by 2 to administrations at 3 weeks interval of the PCPV composition comprising $10^6$ to $10^9$ pfu. In a preferred embodiment, the disease or pathological condition to be treated is a proliferative disease. Accordingly, the present invention also relates to a method for inhibiting tumor cell growth comprising administering the composition of the present invention to a subject in need thereof. In the context of the invention, the methods and use according to the invention aim at slowing down, curing, ameliorating or controlling the occurrence or the progression of the targeted disease.

A "disease" (and any form of disease such as "disorder" or "pathological condition" and the like) is typically characterized by identifiable symptoms. Exemplary diseases include, but are not limited to, infectious diseases that result from an infection with a pathogenic organism (e.g. bacteria, parasite, virus, fungus, etc) and proliferative diseases involving abnormal proliferation of cells. As used herein, the term "proliferative disease" encompasses any disease or pathological condition resulting from uncontrolled cell growth and spread including cancers and some cardiovascular diseases (e.g. restenosis that results from the proliferation of the smooth muscle cells of the blood vessel wall, etc.). The term "cancer" may be used interchangeably with any of the terms "tumor", "malignancy", "neoplasm", etc. These terms are meant to include any type of tissue, organ or cell, any stage of malignancy (e.g. from a pre-lesion to stage IV) and encompass solid tumors and blood borne tumors as well as primary and metastatic cancers.

Representative examples of cancers that may be treated using the composition and methods of the invention include, without limitation, carcinoma, lymphoma, blastoma, sarcoma, and leukemia and more particularly bone cancer, gastrointestinal cancer, liver cancer, pancreatic cancer, gastric cancer, colorectal cancer, esophageal cancer, oro-pharyngeal cancer, laryngeal cancer, salivary gland carcinoma, thyroid cancer, lung cancer, cancer of the head or neck, skin cancer, squamous cell cancer, melanoma, uterine cancer, cervical cancer, endometrial carcinoma, vulvar cancer, ovarian cancer, breast cancer, prostate cancer, cancer of the endocrine system, sarcoma of soft tissue, bladder cancer, kidney cancer, glioblastoma and various types of the central nervous system (CNS), etc. In one embodiment the methods and use according to the present invention is for treating a cancer selected from the group consisting of renal cancer (e.g. clear cell carcinoma), prostate cancer (e.g. hormone refractory prostate adenocarcinoma), breast cancer (e.g. metastatic breast cancer), colorectal cancer, lung cancer (e.g. non-small cell lung cancer) liver cancer (e.g. hepatocarcinoma), gastric cancer, bile duct carcinoma, endometrial cancer, pancreatic cancer and ovarian cancer cancers and a cancer that overexpresses MUC1. Preferred embodiments are directed to a PVPC encoding the MUC1 antigen as described herein for use for treating a subject having a non-small cell lung cancer (NSCL) and a PVPC encoding the HPV16 E7 antigen as described herein for use for treating a subject having a HPV-positive cancer such as a cervix cancer or a head and neck cancer.

Representative examples of infectious diseases that may be treated using the composition and methods of the invention include, without limitation, a) viral diseases such as those resulting from infection by an herpes virus (HSV1, HSV2, or VZV), a papillomavirus (HPV), a poxvirus causing variola or chicken pox, an enterovirus, a retrovirus such as HIV causing AIDS, a cytomegalovirus, a flavivirus (e.g. causing Japanese encephalitis, hepatitis C, dengue and yellow fever), an Hepadnavirus (e.g. HBV), an orthomyxovirus (e.g. influenza virus), a paramyxovirus (e.g. parainfluenzavirus, mumps virus, measles virus and respiratory syncytial virus (RSV)), a coronavirus (e.g. SARS), rhabdovirus and rotavirus; b) diseases resulting from infection by bacteria, for example, *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella*; and (c) fungal diseases including but not limited to candidiasis, aspergillosis, histoplasmosis, cryptococcal meningitis; and d) parasitic diseases including but not limited to malaria, *Pneumocystis carnii* pneumonia, leishmaniasis, cryptosporidiosis, toxoplasmosis, and trypanosome infection.

Typically, upon administration according to the modalities described herein, the composition of the invention provides a therapeutic benefit to the treated subject which can be evidenced by an observable improvement of the clinical status over the baseline status or over the expected status if not treated. An improvement of the clinical status can be easily assessed by any relevant clinical measurement typically used by physicians or other skilled healthcare staff. In the context of the invention, the therapeutic benefit can be transient (for one or a couple of months after cessation of administration) or sustained (for several months or years). As the natural course of clinical status which may vary considerably from a subject to another, it is not required that the therapeutic benefit be observed in each subject treated but in a significant number of subjects (e.g. statistically significant differences between two groups can be determined by any statistical test known in the art, such as a Tukey parametric test, the Kruskal-Wallis test the U test according to Mann and Whitney, the Student's t-test, the Wilcoxon test, etc).

When the method or use of the invention is aimed at treating a proliferative disease, in particular cancer, a therapeutic benefit can be evidenced at least temporarily by for instance a reduction in the tumor number; a reduction of the tumor size, a reduction in the number or extent of metastases, an increase in the length of remission, a stabilization (i.e. not worsening) of the state of disease, a delay or slowing disease progression or severity, a prolonged survival, a better response to the standard treatment, an improvement of quality of life, a reduced mortality, etc. "Treating" can also mean prolonging survival of a subject beyond that expected in the absence of treatment.

When the method or use of the invention is aimed at treating an infectious disease, a therapeutic benefit can be evidenced by for instance, a decrease of the amount of the infecting pathogenic organism quantified in blood, plasma, or sera of a treated subject, and/or a stabilized (not worsening) state of the infectious disease (e.g. stabilization of conditions typically associated with the infectious disease such as inflammatory status), and/or the reduction of the level of specific seric markers (e.g. decrease of alanine aminotransferase (ALT) and/or aspartate aminotransferase (AST) associated with liver poor condition usually observed in chronic hepatitis C), decrease in the level of any antigen associated with the occurrence of an infectious disease and/or the appearance or the modification of the level of antibodies to the pathogenic organism and/or an improved response of the treated subject to conventional therapies (e.g. antibiotics) and/or a survival extension as compared to expected survival if not receiving the composition treatment.

The appropriate measurements such as blood tests, analysis of biological fluids and biopsies as well as medical imaging techniques can be used to assess a clinical benefit. They can be performed before the administration (baseline) and at various time points during treatment and after cessation of the treatment. For general guidance, such measurements are evaluated routinely in medical laboratories and hospitals and a large number of kits are available commercially (e.g. immunoassays, quantitative PCR assays).

In another aspect, the composition of the invention is used or administered for eliciting or stimulating and/or redirecting an immune response in the treated subject. Accordingly, the present invention also encompasses a method for eliciting or stimulating and/or re-orienting an immune response (e.g. to tumor or infected cells) comprising administering the composition of the invention to a subject in need thereof, in an amount sufficient according to the modalities described herein so as to activate the subject's immunity. The elicited, stimulated or redirected immune response can be specific (i.e. directed to epitopes/antigens) and/or non-specific (innate), humoral and/or cellular, notably a CD4+ or CD8+-mediated T cell response. The ability of the composition described herein to elicit, stimulate or redirect an immune response can be evaluated either in vitro (e.g. using biological samples collected from the subject) or in vivo using a variety of direct or indirect assays which are standard in the art (see for example Coligan et al., 1992 and 1994, Current Protocols in Immunology; ed J Wiley & Sons Inc, National Institute of Health or subsequent editions). Those cited above in connection with the antigenic nature of a polypeptide are also appropriate.

In preferred embodiments, the method according to the invention, results in at least one the following properties:
The secretion of high levels of IFN-alpha from PBMC, preferably at levels at least 50-fold higher than the levels observed following administration of a MVA under the same conditions or at levels at least 10 fold higher than the levels observed following administration of a ORFV under the same condition;
The activation of monocyte-derived dendritic cells (e.g. can be reflected by the induction of the activation marker CD86, preferably at levels at least twice the levels observed following administration of a MVA under the same conditions);
The induction of T cell activation or proliferation (e.g. as indirectly reflected by highly granzyme B+ T cells);
A better cytokine/chemokine profile in MDSC (e.g. can be reflected by higher levels of at least one of IFN-alpha and MIP1alpha secreted by MDSC following infection of PCPV than after infection with MVA);
activation of APC (e.g. can be reflected by the upregulation of CD86 in human macrophages following administration of PCPV);
a M2 to M1 conversion of human macrophages (e.g. can be reflected by higher secretion of IL-18, IL-6 and IP-10 in human macrophages after administration of PCPV than after infection with MVA; and/or
- The induction of immunity through a TLR9-mediated pathway or other innate immunity-stimulating pathways such as cGAS-STING and RIG-I-like receptors (RLRs) (e.g., Retinoic acid-inducible gene I (RIG-I) and Melanoma differentiation-associated gene 5 (MDA5)).

Accordingly, the present invention also encompasses methods for increasing secretion of IFN-alpha from an immune cell such as PBMC, for inducing the activation of monocyte-derived dendritic cells, for inducing activation and/or proliferation of T cell, for inducing M2 to M1 conversion of human macrophages, for reducing MDSC-associated immune suppression and/or for reducing immune suppression, any of such methods comprising administering the composition of the invention to a subject in need thereof (in vivo method) or contacting a precursor cell with the composition of the invention (in vitro method) so as to achieve the desired result(s).

In one embodiment, the composition or methods of the invention can be used or carried out in conjunction with one or more other therapeutic agents which are available for treating or preventing the disease or pathological condition to be treated or prevented. In one embodiment the other therapeutic agent is selected from the group consisting of surgery, radiotherapy, chemotherapy, cryotherapy, hormonal therapy, toxin therapy, immunotherapy, cytokine therapy, targeted cancer therapy, gene therapy, photodynamic therapy and transplantation, etc. A method or use according to the invention may include a third or even further therapeutic agent.

Such additional anticancer therapy/ies is/are administered to the subject in accordance with standard practice before, after, essentially concurrently or in an interspersed manner with the PCPV composition of the present invention. Essentially concurrent administration of two or more therapeutic agents does not require that the agents be administered at the same time or by the same route, as long as there is an overlap in the time period during which the agents are exerting their therapeutic effect. Concurrent administration includes administering the composition of the invention within the same day (e.g. 0.5, 1, 2, 4, 6, 8, 10, 12 hours) as the other therapeutic agent. Although any order is contemplated by the present invention, it is preferred that the composition of the invention be administered to the subject before the other therapeutic agent.

In specific embodiments, the method or use according to the invention may be carried out in conjunction with surgery. For example, the composition may be administered after partial or total surgical resection of a tumor (e.g. by local application within the excised zone, for example).

In other embodiments, the method or use according to the invention can be used in association with radiotherapy. Those skilled in the art can readily formulate appropriate radiation therapy protocols and parameters (see for example Perez and Brady, 1992, Principles and Practice of Radiation Oncology, 2nd Ed. JB Lippincott Co; using appropriate adaptations and modifications as will be readily apparent to those skilled in the field). The types of radiation that may be used notably in cancer treatment are well known in the art and include electron beams, high-energy photons from a linear accelerator or from radioactive sources such as cobalt or cesium, protons, and neutrons. Dosage ranges for radio-isotopes vary widely, and depend on the half-life of the isotope, the strength and type of radiation emitted, and the uptake by the neoplastic cells. Regular X-rays doses for prolonged periods of time (3 to 6 weeks), or high single doses are contemplated by the present invention.

In certain embodiments of the invention, the composition of the invention may be used in conjunction with chemotherapy. Representative examples of suitable chemotherapy agents currently available for treating cancer include, without limitation, alkylating agents, topoisomerase I inhibitors, topoisomerase II inhibitors, platinum derivatives, inhibitors of tyrosine kinase receptors, cyclophosphamides, antimetabolites, DNA damaging agents and antimitotic agents. Representative examples of suitable chemotherapy agents currently available for treating infectious diseases include among other antibiotics, antimetabolites, antimitotics and antiviral drugs (e.g. interferon alpha).

In further embodiments, the composition of the invention may be used in conjunction with immunotherapeutics such as anti-neoplastic antibodies as well as siRNA and antisense polynucleotides. Representative examples include among others monoclonal antibodies blocking specific immune checkpoints such as anti-PD-1, anti-PD-L1, anti-CTLA-4, anti-LAG3, anti-OX40 etc (e.g. Ipilimumab, tremelimumab pembrolizumab, nivolumab, pidilizumab, durvalumab. daclizumab, avelumab, atezolizumab, etc.,), monoclonal antibodies blocking Epidermal Growth Factor Receptor (in particular cetuximab, panitumumab, zalutumumab, nimotuzumab, matuzumab, trastuzumab (Herceptin™), etc.,) and monoclonal antibodies blocking Vascular Endothelial Growth Factor (in particular bevacizumab and ranibizumab).

In still further embodiments, the composition of the present invention may be used in conjunction with adjuvant. Representative examples of suitable adjuvants include, without limitation, TLR3 ligands (Claudepierre et al., 2014, J. Virol. 88(10): 5242-55), TLR9 ligands (e.g. CpGs such as ODN1826 (Fend et al., 2014, Cancer Immunol. Res. 2, 1163-74) and Litenimod (Li28) (Carpentier et al., 2003, Frontiers in Bioscience 8, e115-127; Carpentier et al., 2006, Neuro-Oncology 8(1): 60-6; EP 1 162 982; U.S. Pat. Nos. 7,700,569 and 7,108,844) and PDE5 inhibitors such as sildenafil (U.S. Pat. Nos. 5,250,534, 6,469,012 and EP 463 756).

In additional embodiments, the composition or methods of the invention may be used according to a prime boost approach which comprises sequential administrations of a priming composition(s) and a boosting composition(s). Typically, the priming and the boosting compositions use different vectors which comprise or encode at least an antigenic domain in common. Moreover, the priming and boosting compositions can be administered at the same site or at alternative sites by the same route or by different routes of administration. A preferred prime boost approach in the context of the invention involves a PCPV composition as described herein and a MVA composition encoding the same polypeptide of interest (e.g. the same antigen). In one embodiment, the MVA is used for priming and the PCPV composition of the invention is used for boosting or vice versa (PCPV for priming and MVA for boosting). The present invention encompasses one or several administration(s) of the priming and/or the boosting composition(s) with a preference for subcutaneous, intratumoral and intravenous routes. A particularly preferred prime boost regimen comprises a PCPV priming composition administered by intratumoral route and a MVA boosting composition administered by intravenous route. In a preferred embodiment, the PCPV and MVA composition encodes the same tumor-associated antigen. In another embodiment, the period of time separating the administrations of the priming and the boosting varies from one week to 6 months, with a preference for one week to one month and even more for a period of one to two weeks. Individual doses of approximately $10^6$ pfu to approximately $10^9$ pfu are particularly adapted for priming and boosting compositions and notably individual doses of approximately $10^6$, $5 \times 10^6$ $10^7$, $5 \times 10^7$, $10^8$ or $5 \times 10^8$ pfu.

In another aspect, the present invention also provides a bovine papular stomatitis virus (BPSV), preferably a recombinant BPSV comprising at least one foreign nucleic acid inserted in its genome. The term "bovine papular stomatitis virus" or "BPSV" is used herein according to its plain ordinary meaning within Virology and refers to a member of the Poxviridae family belonging to the Parapoxvirus genus.

The foreign nucleic acid(s) to be expressed by the recombinant BPSV is/are similar to those described in connection with PCPV as well as the regulatory elements required for expression in a desired host cell or subject. Insertion site(s) of the foreign nucleic acid(s) within the BPSV genome and method of producing recombinant BPSV are also within the reach of the person skilled in the art. Method for amplifying BPSV is routine based on the description given herein for the PCPV virus and general knowledge, although producer cell lines, MOI, culture medium, etc can be adapted to the BPSV virus by the skilled artisan.

Composition comprising a therapeutically effective amount of the BPSV and a pharmaceutically acceptable vehicle are also part of this invention. Suitable dosages, administration routes and therapeutic uses are as described above for PCPV-comprising compositions.

All of the above cited disclosures of patents, publications and database entries are specifically incorporated herein by reference in their entirety. Other features, objects, and advantages of the invention will be apparent from the description and drawings and from the claims. The following examples are incorporated to demonstrate preferred embodiments of the invention. However, in light of the present disclosure, those skilled in the art should appreciate that changes can be made in the specific embodiments that are disclosed without departing from the spirit and scope of the invention.

EXAMPLES

Several viruses and strains have been developed to express tumor antigens and cytokines, and some of them are in advanced clinical trials. However, novel viral strains with improved immunogenic properties are sought. In this perspective, we screened Parapoxviruses such as Pseudocowpox (PCPV) and Parapoxvirus Ovis (ORF) and compared them to a variety of other poxviruses. The comparison was conducted in vitro with human primary immune cells, and in vivo with syngeneic mouse tumor models.

Example 1: Profile of Secreted Cytokines/Chemokines in Infected Human Peripheral Blood Mononuclear Cells (PBMCs)

Human peripheral blood mononuclear cells (PBMCs) were isolated from whole human blood of two healthy donors (EFS, Etablissement de Strasbourg; donor A and B). PBMCs were isolated by density gradient centrifugation using Ficoll-Paque PLUS (GE HealthCare) and Blood Separation Tubes (Greiner) and stored in liquid nitrogen.

Frozen aliquots of PBMCs were thawed in RPMI supplemented with 10% Fetal calf serum (FSC) and dispatched in 24 well plates ($5 \cdot 10^5$ cells in 500 µL/well). After 5 to 6 hours, cells were infected with the different viruses (see below) at multiplicities of infection (MOI) between $10^{-3}$ and 10. After overnight incubation (16 hours), cells were scraped, cells and supernatant were transferred in Eppendorf tubes and centrifuged 10 min at 300 g. Supernatant was isolated and frozen at −80° C. Cytokine and chemokine profiles were quantified by a Multiplex approach in the supernatants using a Procartaplex 20plex inflammation panel (EPX200-12185-901). The analysis was carried out according to the manufacturer's recommendation using a MagPix device.

The different viruses tested are Parapoxviruses pseudo-cowpoxvirus (PCPV and Parapoxvirus ovis (ORF), as well as MVA, cowpox virus (CPX), Copenhagen vaccinia virus (Copwt), fowlpox (FPV), Myxomavirus (MYXV), Swine pox (SWPV), raccoonpoxvirus (RCN), Cotia virus (CTV) and Yaba-like disease virus (YLDV). The viruses were obtained from the ATCC collection, respectively ATCC-VR-644 (PCPV TJS), ATCC VR-1548 (ORFV NZ2), ATCC VR-302 (CPX Brighton), ATCC VR-115 (MYXV Lausanne), ATCC VR-363 (SWPX Kasza), ATCC VR-838 (RCN Herman), ATCC VR-464 (CTV SPAN 32) and ATCC VR-937 (YLDV Davis); except MVA for which an empty MVA vector named MVAN33 was used (Genbank accession number EF675191), the Copenhagen vaccinia virus (see e.g. WO2009/065546) and FPV (see e.g. Laidlaw and Skinner, 2004; J. Gen. Virol., 85: 305-22).

As shown in FIG. 1, PCPV-infected PBMCs induced the secretion of very high levels of IFN-alpha in a MOI-dependent way. Although the levels secreted by the PCPV-infected PBMC vary between the two experiments, they are well above the moderate secretion levels of IFN-alpha observed with SWPX and ORFV (another parapoxvirus). Compared with MVA, PCPV induced a 1000-fold higher expression of IFN-alpha in human PBMCs whereas SWPX and ORF displayed a lower 10 to 100-fold induction. Copenhagen VV and other oncolytic vectors (e.g. RCN, RPV, CTV, CPX and MYX) did not raise the IFN alpha level.

Viability studies upon viral infection were carried out. Cells were stained with LiveDead "NearIR" and analyzed by flow cytometry (MacsQuant) to determine the proportion of dead and living cells. The results showed that ORFV and YLDV were particularly toxic: 90% of cells infected at the MOI of 5 died within 16 hours, while at least 50% of living cells were observed for all other viruses, including PCPV.

Example 2: Effect of PCPV on Human Monocyte-Derived Dendritic Cells, M2 Macrophages and Myeloid-Derived Suppressor Cells (MDSCs)

Type I interferons like IFN-alpha are key players in immunotherapy of cancer as well as altered immunosuppressive tumor environment and improved adaptive anti-tumor responses against vaccine encoded and/or tumor-presented antigens as described e.g. by Parker et al. (2016, Nat Rev Cancer 16(3): 131-44) and Zitvogel et al. (2015, Nat Rev Immunol. 15(7): 405-14) To address these aspects, we looked in vitro in human primary immune cells at the activation of human monocyte-derived dendritic cells (moDC) and at the effect on immunosuppressive cell populations (re-programming of immunosuppressive cells like M2 macrophages and MDSCs) upon PCPV treatment. Preclinical studies on innate and adaptive immunity were also probed in murine syngeneic tumor models.

Stimulation of moDCs.

Figure 2:
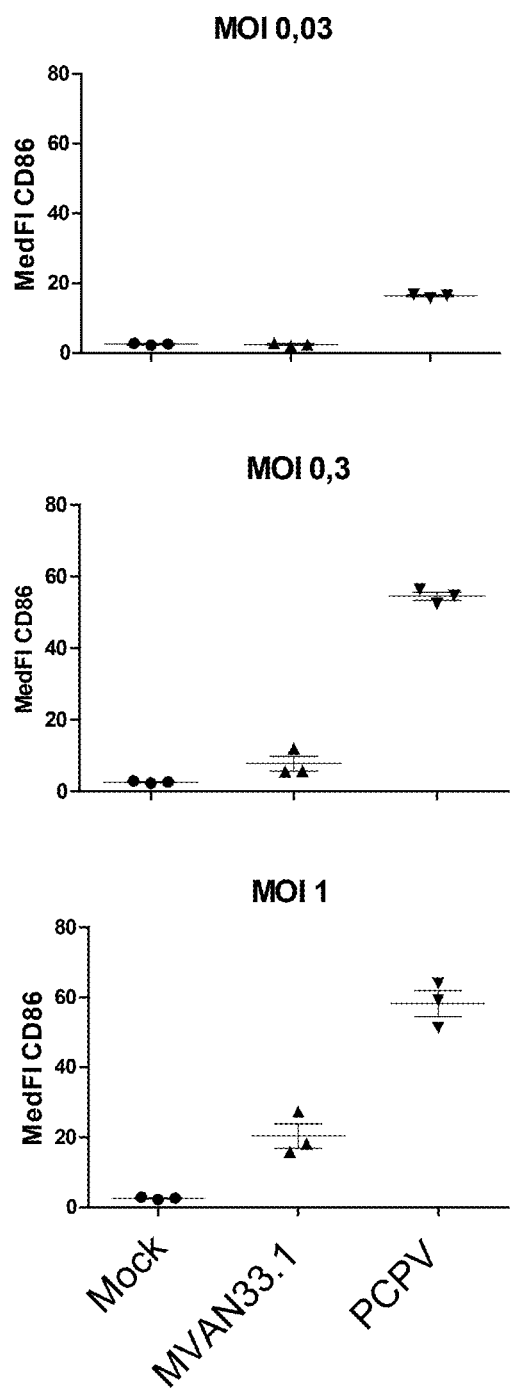
FIG. 2 illustrates expression levels of the activation marker CD86 measured by flow cytometry in virus-infected moDCs obtained from three different donors. Shown is median fluorescence intensity (MedFI) for CD86 in moDCs (3 donors), observed 16 h after infection with the empty MVA vector MVAN33.1 or PCPV at MOI 0.03, 0.3 or 1 or mock as negative control. Expression levels were measured by staining with anti-CD86-PE quantification of the cell-bound signal by flow cytometry.

To probe the activation of antigen-presenting cells (APCs), we worked with monocyte-derived dendritic cells (moDCs). To obtains these cells, human monocytes were enriched by depletion from PBMCs (Miltenyi, Monocyte Isolation kit II). Monocytes were differentiated in dendritic cells (moDCs) by incubation in granulocyte-macrophage colony-stimulating factor (GM-CSF 20 ng/ml) and IL-4 (10 ng/ml) for 3 days. For stimulation assays, moDCs from three different donors (donor 12July16, donor 24August16 and donor 31August16) were plated in 24-well plates and infected with MVAN33.1 or PCPV at the MOIs of 0.03, 0.3 and 1. The day after, the maturation marker CD86 was quantified by flow cytometry. Expression levels were measured by staining with anti-CD86-PE quantification of the cell-bound signal by flow cytometry As illustrated in FIG. 2, PCPV-treated moDCs showed much higher expression levels of the activation marker CD86 compared to MVAN33.1-treated cells. The beneficial effect on moDC stimulation was seen at low MOI (0.03) and increased at MOI 0.3 and 3. As expected, no moDC stimulation was detected upon mock treatment. Therefore, it appeared that PCPV infection increased CD86 expression on all donors at all MOI to higher levels than MVAN33. Copwt had no effect on moDC CD86 expression (data not shown).

Effects on M2 Macrophages

Next, we addressed the question whether and to which extent immunosuppressive cell types could be altered/re-educated by PCPV.

We generated in vitro derived $CD163^+CD206^+$ "M2-type" macrophages according to a protocol adapted from Mia et al. (2014, Scand. J. Immunol. 79(5): 305-14). Briefly, after isolation from PBMCs obtained from healthy donors either by positive CD14+ selection or by negative selection using monocyte isolation kit II (Miltenyi, Biotec), 4×10$^5$ monocytes were cultured on 48 well plates in 500 μl Macrophage Base Medium DXF (Promocell) supplemented with 50 ng/ml M-CSF (Miltenyi Biotec). Medium was changed at day 3 and day 7. At day 7, CD16$^{hi}$CD68$^+$CD11b$^+$ M0 macrophages were polarized towards a M2 phenotype adding IL-4, IL-10 and TGF-beta (Miltenyi Biotec) to a concentration of 20 ng/ml. Two days later, CD163$^+$CD206$^+$ M2 macrophages were incubated with MVAN33.1 or PCPV at a MOI of 5, 1 and 0.3 and the secretion of IL-18, IL-6, IP-10 and CD86 was assayed by flow cytometry or Luminex analysis. For this purpose, cells were incubated for 20 min with human FcR Blocking Reagent (Miltenyi Biotec) and APC-labeled anti-CD86 (clone FM95, Miltenyi Biotec). Dead cells were labeled by automatic propidium iodide staining before cell acquisitions recorded using MACSQuant cytometer (Miltenyi). Data were analyzed using Kaluza software (Beckman Coulter). Cytokines levels in the supernatant of stimulated cells were quantified by Luminex analysis (ProcartaPlex, eBiosciences) on a MAG-PIX device (Luminex XMAP Technologies).

Figure 3:
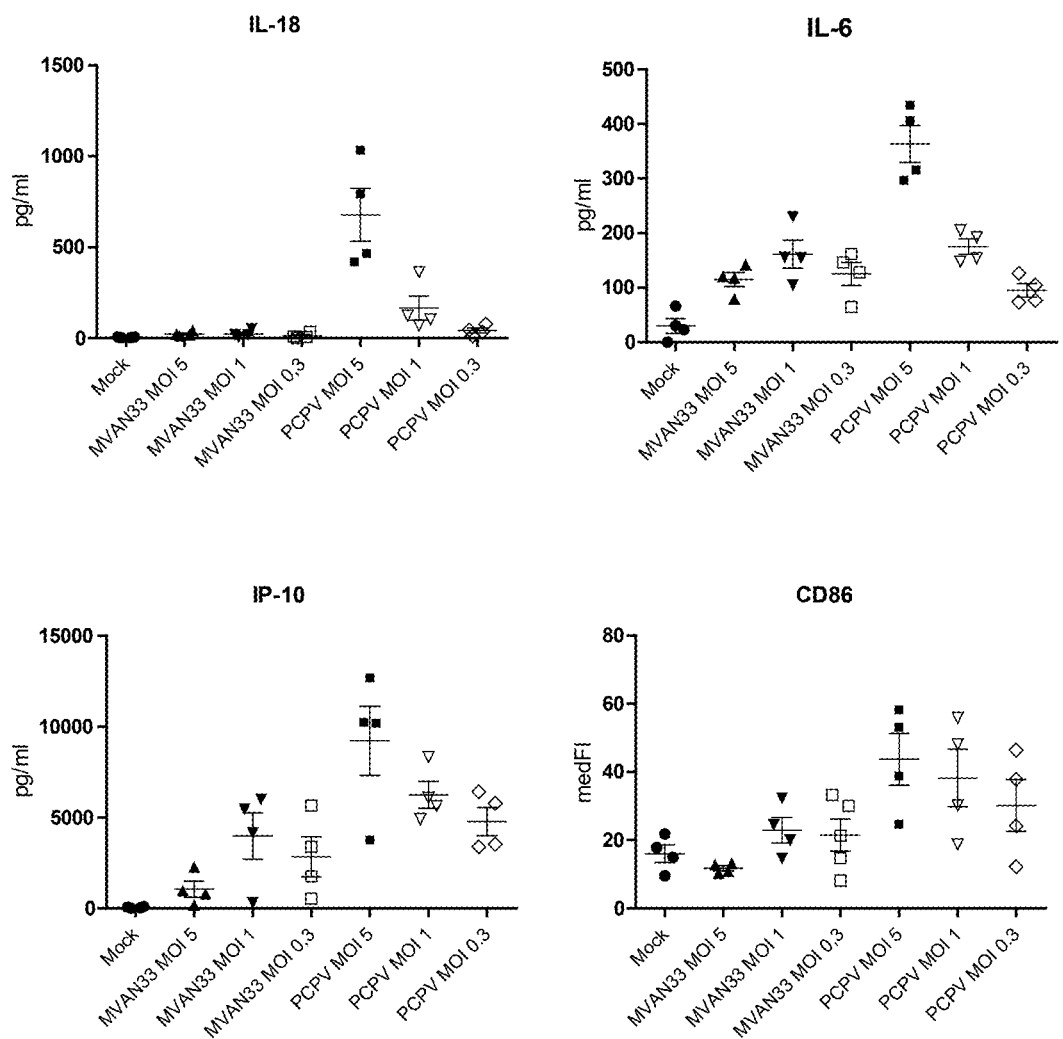
FIG. 3 illustrates the cytokine levels measured by Luminex analysis in the supernatant of CD163+ CD206+ M2 macrophages generated from PBMCs as described herein following incubation with MVAN33.1 or PCPV at MOI 5, 1 and 0.3.

As illustrated in FIG. 3, compared to MVA, PCPV augmented the secretion of IL-18 at MOI 5 and 1, the secretion of IL-6 and IP-10 at MOI 5. Thus, it appeared that PCPV changes the phenotype of M2 macrophages towards a M1-type phenotype. M2 macrophages are associated with a negative outcome in human NSCLC, while M1 macrophages represent a positive prognostic marker (Yuan et al, 2015, Nature, Scientific Reports). These data suggest a conversion to a less suppressive phenotype after PCPV treatment compared to MVA treatment.

Effects on Myeloid-Derived Suppressor Cells MDSCs

Figure 4:
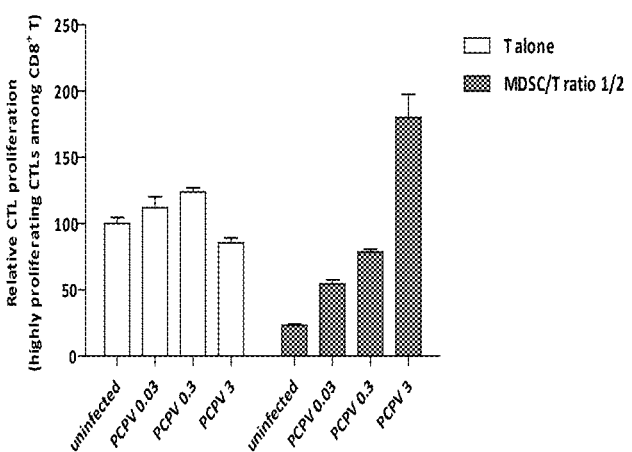
FIG. 4 illustrates A) Relative CTL proliferation alone or in co-culture with MDSCs derived in the presence of 20 ng/ml GM-CSF, 10 ng/ml IL4 and 1 µM prostaglandin E2 (MDSC/T ratio of ½) after treatment with PCPV at MOI 0.03, 0.3 or 3. B) Relative Granzyme B expression in highly proliferating T cells alone or in co-culture with MDSC (co-cultured as indicated in A) treated with PCPV at indicated MOI. C) IFN-alpha secretion after treatment of MDSCs with PCPV overnight at indicated MOI.
Figure 4:
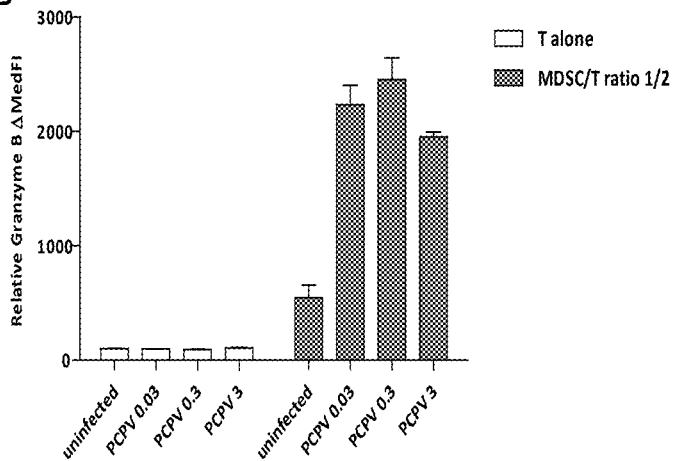
Figure 4:
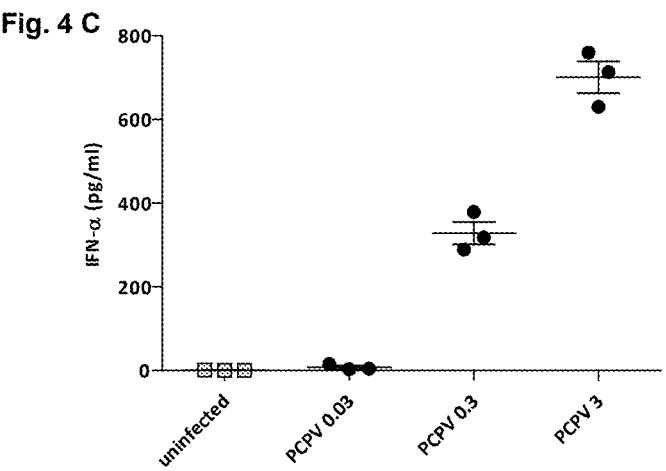

Autologous CD14$^+$ monocytes and CD8$^+$ T cells were isolated from healthy donors by magnetic beads technology (Miltenyi). Two models were investigated. MDSCs were generated from monocytes either by incubation with 20 ng/ml GM-CSF, 10 ng/ml IL-4 and 1 μM prostaglandin E2, (FIG. 4) or in the presence of 10 ng/ml GM-CSF and 10 ng/ml IL-6 (FIG. 5) for 6 to 7 days. The resulting MDSCs were cocultured with autologous CFSE-labeled CD8$^+$ T cells in the presence of T cell activation beads coated with anti-CD2, anti-CD3 and anti-CD28 or TransAct T Cell Reagent+IL-2 (Miltenyi Biotec). After 4-5 days, proliferation of T cells and expression of Granzyme B in proliferating T cells were measured by flow cytometry. In addition, MDSCs alone were treated with PCPV, the next day supernatant was taken to quantify analytes like cytokine and chemokines. As shown in FIG. 4, proliferation of activated T cells was inhibited by co-cultured in vitro-derived MDSCs (see uninfected controls in FIG. 4A; MDSC/T ratio of ½). However, the suppressive activity provided by MDSCs on CTL proliferation can be inhibited after treatment with PCPV added to the co-culture as evidenced by the ability of PCPV to restore CTL proliferation at increasing MOIs (FIG. 4A) correlating with upregulation of Granzyme B production in co-cultures treated with PCPV (FIG. 4B). To be highlighted that the anti-suppressive effect in the presence of PCPV was detected even at low MOI. These observation correlate with IFN alpha secretion measured in MDSCs cultures the day after treatment with PCPV (FIG. 4C).

Figure 5:
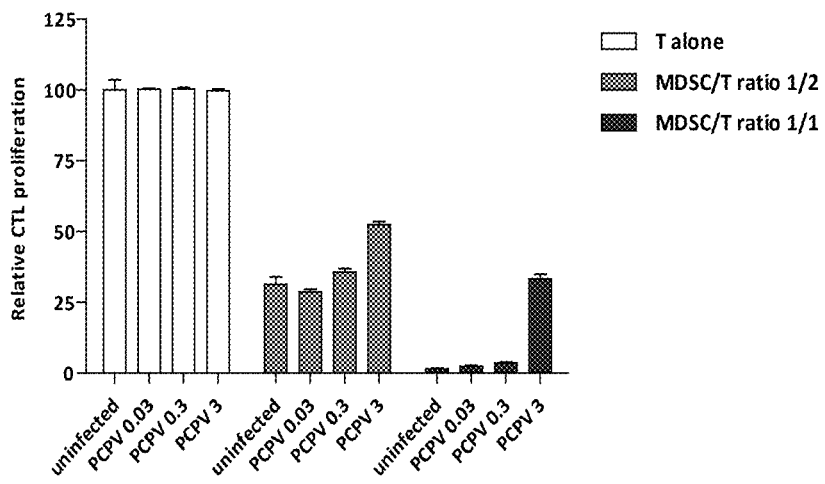
FIG. 5 illustrates A) Relative CTL proliferation alone or in co-culture with MDSCs derived in the presence of 10 ng/ml GM-CSF and 10 ng/ml IL-6 (MDSC/T ratio of ½ and 1/1) after treatment with PCPV at MOI 0.03, 0.3 or 3. B) Relative Granzyme B expression in proliferating T cells alone or in co-culture with MDSC (co-cultured as indicated in A) treated with PCPV at indicated MOI.
Figure 5:
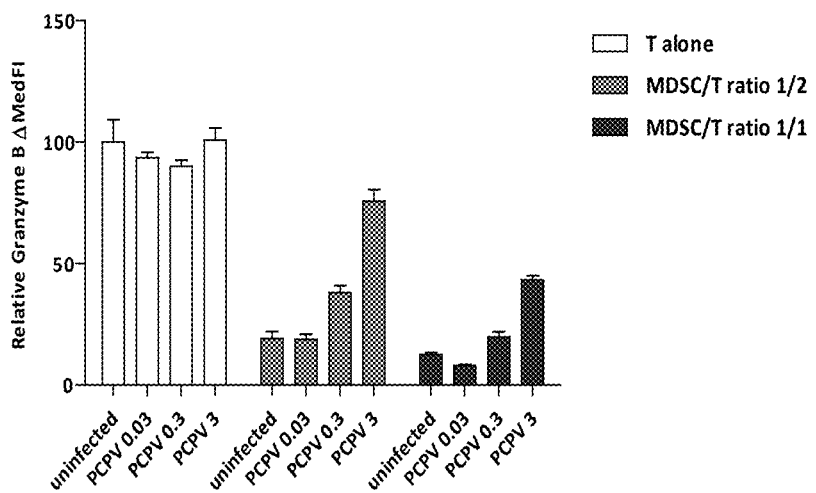

As above, and as shown in FIG. 5 illustrating the GM-CSF, IL-6-derived MDSC model, proliferation of activated T cells was strongly inhibited by co-cultured in vitro-derived MDSCs. Proliferation was partly restored, and Granzyme B expression was upregulated when co-cultures were treated with PCPV at increasing MOIs.

In summary, PCPV was shown to be superior than MVA and VV to trigger the expression of CD86 in primary moDCs. Furthermore, PCPV treatment increased CD86 expression in human in vitro-derived CD163+CD206+ "M2"-type macrophages, suggesting a shift to an antigen-presenting phenotype. In these cells, PCPV increased significantly the secretion of IL-18, IL-6 and IP-10, signing a conversion towards a less suppressive macrophage phenotype. The mode of action of PCPV on MDSCs could be maturation to a less suppressive phenotype or toxic effects of PCPV on MDSCs.

Example 3: Construction of Recombinant PCPV and Anti-Tumor Properties

The interest for PCPV as viral backbone was evaluated by generating recombinant PCPV encoding tumor antigens and testing them in tumor control experiments.

Recombinant PCPV vectors were constructed from the wild-type strain TJS (ATTC, VR-634). PCPV, as all the Parapoxvirus, lack genes present or conserved in other poxviruses. These comprises homologues of most poxviral genes likely involved in nucleotide metabolism, including homologues of ribonucleotide reductase (RR), thymidine kinase (TK), guanylate kinase and thymidylate kinase. Therefore, the locus TK generally used for generation of recombinant vaccinia virus could not be used for introduction of recombinant gene in PCPV. However, it was shown that recombinant ORF virus could be generated by insertion of the transgene in the non-essential VEGF gene (Rziha et al., 2000, J. Biotechnol. 83(1-2): 137-145). This locus was therefore evaluated for the generation of recombinant PCPV. It should be noticed that the VEGF gene is present in two copies in the PCPV genome on the left and right genome terminus.

A transfer plasmid was generated by cloning in pUC18 plasmid (available e.g. in Thermo Fisher Scientific) two sequences of about 300 bp flanking the PCPV VEGF gene. The sequences upstream the VEGF gene correspond to nucleotide position 6391 to 6089 or 138899 to 139201 of PCPV (Genbank NC_013804). The sequences downstream the VEGF gene correspond to nucleotide position 5545 to 5225 or 139745 to 140065 of PCPV. These sequences will allow homologous recombination between the transfer plasmid and PCPV virus leading to recombinant virus with the foreign nucleic acid inserted in both VEGF locus.

Generation of PCP-GFP (PCPTG19106)

The selection cassette (eGFP/GPT), a fusion of the gene encoding the enhanced green fluorescent protein (eGFP) and the gene encoding guanine phosphoribosyl transferase (GPT) (see e.g. WO2009/065546) was positioned under the control of p11K7.5 vaccinia promoter and inserted in the transfer plasmid leading to pTG19106.

Generation of PCPTG19106 was performed by homologous recombination in Bovine Turbinate cells (BT, ATCC CRL-1390) infected with PCPV and transfected by nucleofection with pTG19106 (according to Amaxa Nucleofector technology). Fluorescent and selective (GPT+) plaques were selected. More specifically, GPT$^+$ recombinant PCPV have a growth advantage in a selective medium (mycophenolic acid, xanthine, and hypoxanthine), by maintaining the GPT selection marker during the isolation of recombinant PCPV. Recombinant virus was isolated from GFP-fluorescent plaques and submitted to additional plaques purification in BT cells. Virus structure and absence of parental PCPV was confirmed by multiple PCRs and DNA sequencing of the expression cassette. The resulting virus PCPTG19106 was amplified in BT cells. Virus stocks were titrated on BT cells by plaque assay.

Generation of PCP-mCherry (PCPTG19153)

The sequence coding for the mCherry fluorescent protein was positioned under the control of pH5R vaccinia promoter and inserted in the transfer plasmid leading to pTG19153.

Generation of PCPTG19153 was performed by homologous recombination in BT cells infected with PCPTG19106 and transfected by nucleofection with pTG19153. Recombinant virus was isolated by selected mCherry-fluorescent plaques and submitted to additional plaques purification in BT cells. Virus structure and absence of parental PCPTG19106 was confirmed by multiple PCRs and DNA sequencing of the expression cassette. The resulting virus PCPTG19153 was amplified in BT cells.

Generation of PCP-HPV16E7 (PCPTG19178)

The sequence coding for SR-E7*Tm (WO99/03885) was positioned under the control of p7.5K promoter and inserted in the transfer plasmid leading to pTG19178. Generation of PCPTG19178 was performed by homologous recombination in BT cells infected with PCPTG19106 and transfected by nucleofection with pTG19178 in presence of an endonuclease generating double-strand break in the GFP gene. Recombinant virus was isolated by selected GFP-fluorescent negative plaques and submitted to additional plaques purification in BT cells. Virus structure and absence of parental PCPTG19106 was confirmed by multiple PCRs and DNA sequencing of the expression cassette. The resulting virus PCPTG19178 was amplified in BT cells.

Production of pre-clinical batch of PCPTG19178 was performed by infected Hela cells (ATCC® CCL-2™) in several F500 flasks. Viral amplification was performed at 34 to 37° C., 5% CO2 for 72 h. Infected cells and medium were then pelleted and frozen. The crude harvest was disrupted using high shear homogenizer (SILVERSON L4R) and submitted to a purification process (e.g. as described in WO2007/147528). Briefly, the lysed viral preparation can be clarified by filtration, and purified by a tangential flow filtration (TFF) step. Purified virus was resuspended in a suitable virus formulation buffer (e.g. 5% (w/v) Saccharose, 50 mM NaCl, 10 mM Tris/HCl, 10 mM Sodium Glutamate, pH8).

Generation of PCP-MUC1 (PCPTG19194)

The sequence coding for Muc1 (U.S. Pat. No. 5,861,381) was positioned under the control of pH5R promoter and inserted in the transfer plasmid leading to pTG19194. Generation of PCPTG19194 was performed by homologous recombination in BT cells infected with PCPTG19153 and transfected by nucleofection with pTG19106 in presence of an endonuclease generating double-strand break in the m-Cherry gene. Recombinant virus was isolated by selected mCherry-fluorescent negative plaques and submitted to additional plaques purification in BT cells. Virus structure and absence of parental PCPTG19194 was confirmed by multiple PCRs and DNA sequencing of the expression cassette. The resulting virus PCPTG19194 was amplified in BT cells. Pre-clinical batch were produced in Hela cells as described above.

Generation of PCP-HBV (PCPTG19179)

The sequence coding for a fusion of HBV core Pol and env antigens (as described in WO2013/007772) was positioned under the control of p7.5K promoter and inserted in the transfer plasmid leading to pTG19179. Generation of PCPTG19179 was performed by homologous recombination in BT cells infected with PCPTG19106 and transfected by nucleofection with pTG19179 in presence of an endonuclease generating double-strand break in the GFP gene. Recombinant virus was isolated by selected GFP-fluorescent negative plaques and submitted to additional plaques purification in BT cells. Virus structure and absence of parental virus was confirmed by multiple PCRs and DNA sequencing of the expression cassette.

Tumor Control Experiments in Syngeneic MC38 Model:

The capacity of PCPV to control tumor growth and to increase survival rates was probed in the colon carcinoma cell line MC38 ($2\times10^6$ cells) (available from Kerafast) injected subcutaneously in syngeneic C57BL/6 mice shaved beforehand. The injection site was labeled with a permanent marker. Day 2, $1\times10^7$ pfu of HPV-16 E7-encoding PCPV or a MVA virus, or buffer were injected at the cell line injection site (D2) and later in the emerging tumor at day 9 and 16 (D9 and D16). Ten mice per group were injected. Tumor growth and survival were monitored over one month following MC38 cell implantation. The administration protocol is illustrated in FIG. 6A.

Figure 6:
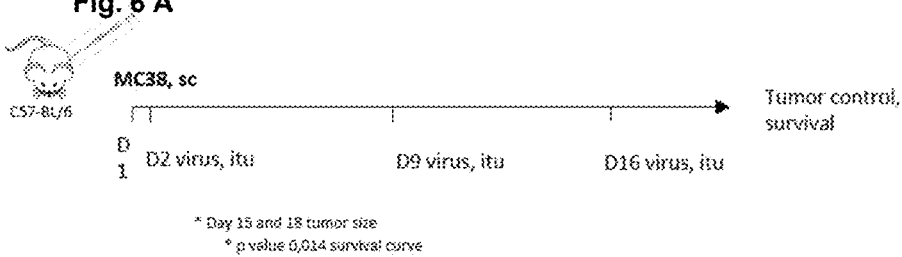
FIG. 6 illustrate the evolution of tumor growth and animal survival in MC38 tumor model. The animals were divided in three groups of ten mice. For all groups, syngeneic C57BL/6 mice were injected subcutaneously with $2·10^6$ MC38 cells according to the protocol shown in (A). The injection site was labeled with a permanent marker. The animal received three intratumoral injections of $1·10^7$ pfu of MVA-HPV16E7m (B) or PCPV-HPV16E7m (C) or buffer (D), respectively 2 days after cell implantation (at the cell line injection site) and in the emerging tumor at day 9 and 16. Tumor growth was estimated by measuring tumor volumes over time. (E): Overall survival (OS) rates represented as Kaplan-Meier curves. Solid line (-) represents animal group treated with MVA-HPV16E7m (MVATG14197), dashed line (- -) the group treated with PCPV-HPV16E7m (PCPV19178) and dotted line (..) the one treated with buffer (S08).
Figure 6:
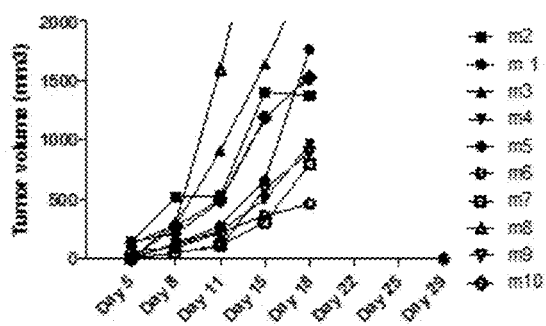
Figure 6:
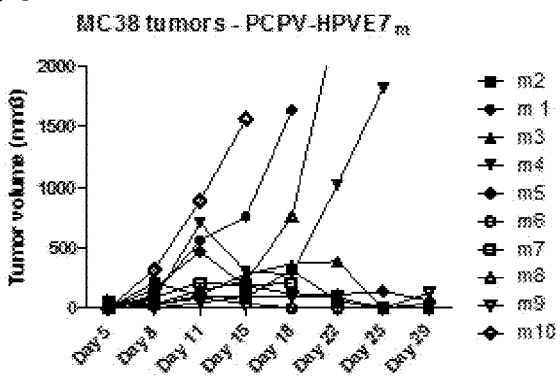
Figure 6:
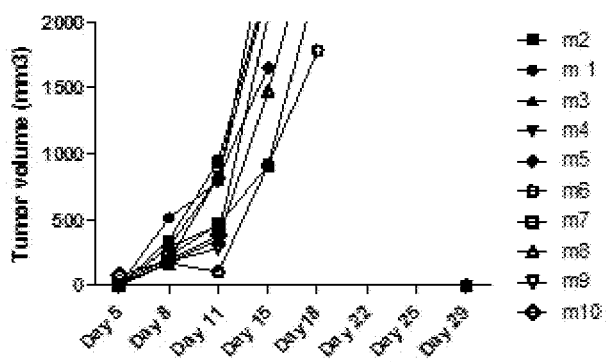
Figure 6E:
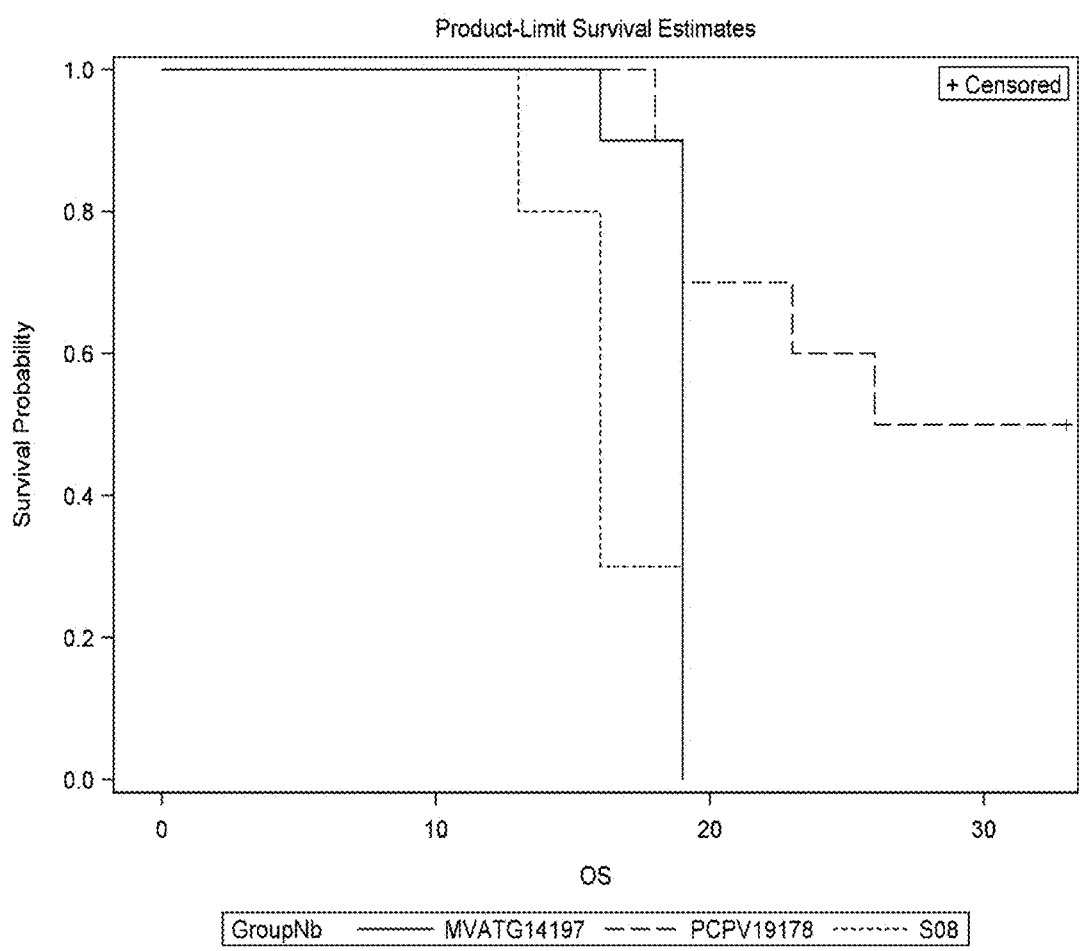

In all animals treated with buffer, tumors grew rapidly beyond the volume of 1500 mm$^3$ within the 11 to 18 days following MC38 implantation (FIG. 6D). In contrast, animals treated with the recombinant HPV16E7-encoding MVA showed a delay in tumor growth. More specifically, tumors exceeding 1500 mm$^3$ at day 18 were observed in 5/10 whereas tumor growth is moderate in the 5 others (<1000 mm$^3$ at day 18 post tumor implantation) as illustrated in FIG. 6B. Surprisingly, PCPV treatment provides a stronger antitumoral protection as compared to MVA treatment. Indeed, tumors reaching a volume of 1500 mm$^3$ were observed in only 4/10 animals after 15 to 24 days post tumor implantation and no tumor growth was seen in the 6 others (FIG. 6C). On the same line, PCPV increased survival in the treated animals (FIG. 6E)

In conclusion, when injected intratumorally into fast growing MC38 tumors, PCPV injection led to tumor growth control and increased survival compared to buffer or MVA injected animals.

Depletion Experiments

The tumor control experiment in MC38-bearing mice was repeated, but depletion of specific cell populations, respectively CD4+, CD8+ and neutrophils, was applied with appropriate depleting antibodies injected before and during PCPV treatment. More specifically, depletion of CD8$^+$ cells was carried out by intraperitoneal (ip) injection of 200 µg of a rat monoclonal antibody (MAb) anti-mouse CD8 (clone 53-6-7; BioXCell) at days −1, −2, 6 and 13. Depletion of CD4$^+$ cells resulted from intraperitoneal injection of 200 µg of a rat Mab against mouse CD4 (clone GK1.5 available at BioXCell) at days −1, −2, 6 and 13. Depletion of neutrophils (and other Ly6G cells) was made according to the protocol described in Wozniak et al. (2012, BMC Immunology, 13:65), using a rat MAb against mouse Ly6G (clone 1A8; BioXCell) injected ip at a dose of 200 µg day −2 and then every other day or every three days over the week end.

As described above, the colon carcinoma cell line MC38 ($2\times10^6$ cells) was injected subcutaneously in syngeneic C57BL/6 mice shaved 2 days before. The injection site was labeled with a permanent marker. One$10^7$ pfu of PCPV or buffer (negative control) were injected day 2 at the cell line injection site and later in the emerging tumor (days 9 and 16). 13 mice per group were injected.

Depletion of CD4$^+$, CD8$^+$ and Ly6G$^+$ cells was confirmed in blood and spleen (periphery) from mice sacrificed at day 14 (data not shown). However, the absence of neutrophils in MC38 tumors from mice treated with Ly6G could not be demonstrated (Myeloperoxidase MPO signal remained detectable). Reduction of neutrophil counts could not be evidenced due to the lack of quantitative measures. Depletion of CD4+ and CD8+ cells in tumors could not be probed for technical reasons.

Figure 12:
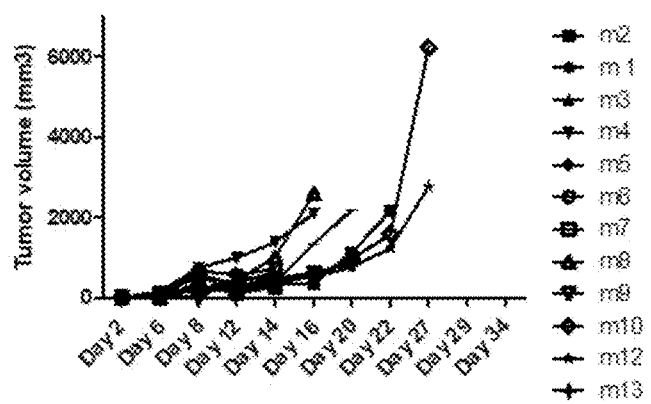
FIG. 12 illustrates a tumor control experiment in MC38-bearing mice upon intratumoral injection of $1×10^7$ pfu of PCPV (A) or buffer (E) and intraperitoneal injection of depleting antibodies anti-Ly6G (B), anti-CD8 (C) and anti-CD4 (D) to deplete mouse neutrophils, CD8+ cells and CD4+ cells, respectively. Each group comprise 13 mice.
Figure 12:
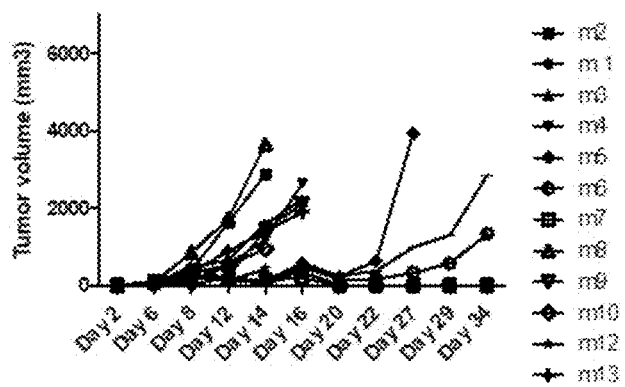
Figure 12:
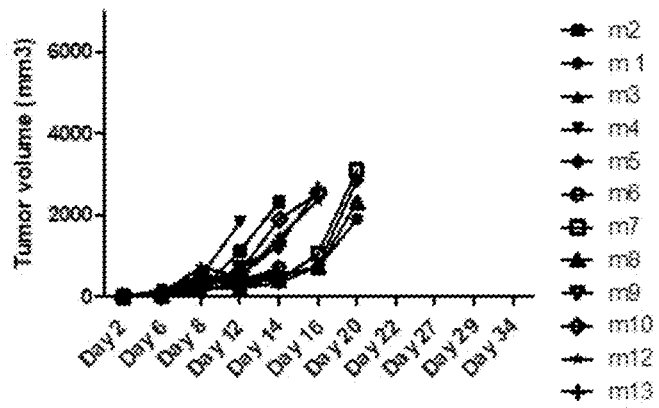
Figure 12:
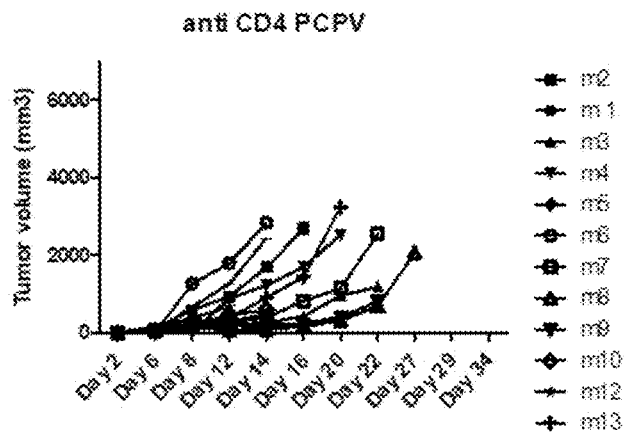
Figure 12:
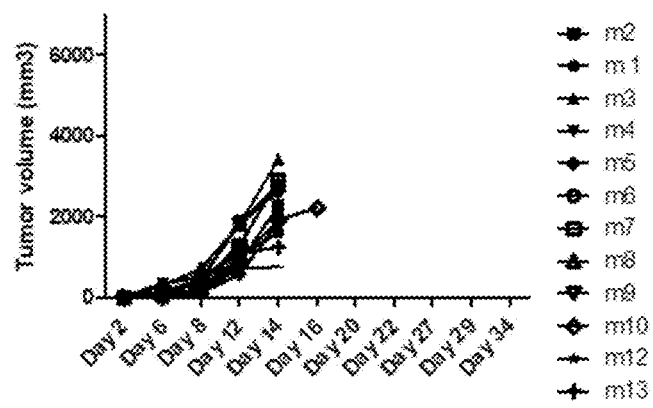

As expected, tumors grow rapidly in buffer treated animal (FIG. 12E) whereas treatment with PCPV delayed tumor growth (FIG. 12A). Tumor size was even more controlled between days 16 and 29 in group treated with PCPV and anti Ly6G (FIG. 12B) with respect to the group treated with PCPV alone (p-value <0.001). Treatment with PCPV and anti CD8 led to bigger tumor sizes compared to the PCPV-treated group (p-value 0.05) (FIG. 12C) whereas treatment with CD4-depleting antibody did not show significant effect on tumor growth (FIG. 12D). In addition, treatment with PCPV and anti CD8 decreased survival, while the treatment with PCPV and anti Ly6G increased survival (p-value 0.001).

The results suggest a role for CD8+ cells in PCPV-induced antitumoral response. Treatment with Ly6G increases survival, most likely due to the depletion of circulating MDSCs and N2 neutrophils. Shaul and Fridlender (2017, J. Leuko. Biol. 102(2): 343-9), described the functional plasticity of neutrophils (pro-tumor (N2) and anti-tumor (N1) nature of neutrophils which infiltrate in the tumor under the influence of specific cytokines.

Induction of Tumor-Specific T Cells in Long Term Survivors

The presence of MC-38-specific T cells was investigated in long-term mice survivors with reduced/resolved MC38 tumors at day 34 and compared to naive animals. Splenocytes were isolated and processed essentially as follows. Spleens from 5 survivor animals were collected and pooled (PCPV survivor pool) or individual spleen of 2 survivor mice was collected in Complete medium (CM) and then crushed with a syringe plunger. Splenocyte suspension was diluted in CM, laid over 4 mL of Lympholyte®-M separation cell media (Cedarlane). The interphase containing lymphocytes was collected by centrifugation and resuspended in RBC lysis buffer (BD PharmLyse, BD BioScience) till lysis of red blood cells (RBC) occurs. Lymphocytes were resuspended in CM and counted (Beckman Coulter) Cell concentration was adjusted to $1 \times 10^7$ cells per mL with CM. Stimulation was performed with MC38 cells treated with Mitomycin C, cells stimulated with medium (negative control) or the irrelevant peptide i8L (negative control). ELISpot analysis for antigen-specific IFN-gamma (IFNg) producing splenocytes was carried out according to standard protocol.

Figure 13:
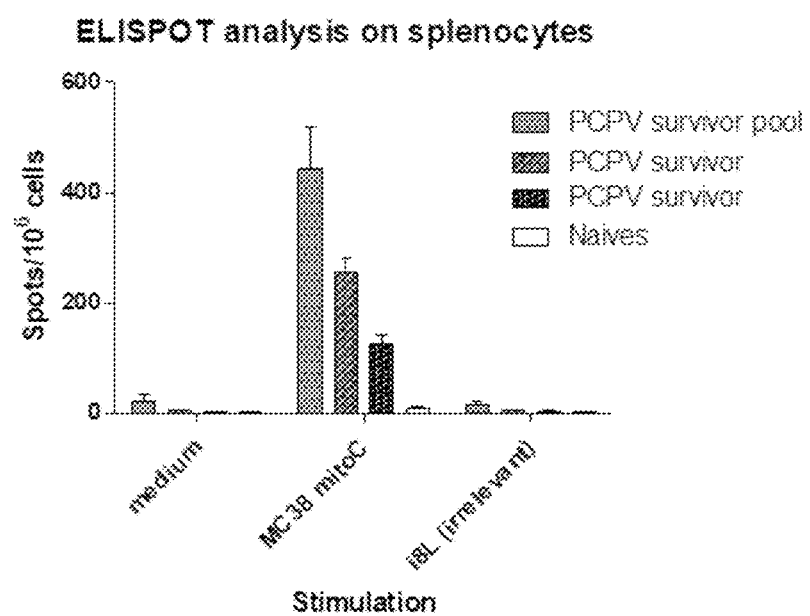
FIG. 13 illustrates ELISPOT analysis on splenocytes from survivor mice having received PCPV injections and showing reduced or resolved MC38 tumors at day 34. Spleens from 5 survivor animals (PCPV survivor pool) and of two individual survivors (PCPV survivor) and of naïve mice (Naives) were collected to isolate lymphocytes from the splenocyte suspensions. One$10^7$ cells per mL were plated in ELISA plates and stimulated with Mitomycin C-treated MC38 cells or irrelevant I8L peptide or with complete medium (medium). Spots were counted with an ELISPOT reader (CTL Immunoqpot reader). Each condition was tested in quadriplate and the results expressed as the mean number of spot-forming units (sfu) per $1\times10^6$ splenic lymphocytes.

FIG. 13 illustrates that after PCPV treatment, tumor-specific (MC-38)-specific T cells were detected in splenocytes of pooled or individual survivor mice (having reduced/resolved MC38 tumors at day 34) after stimulation with MC 38 cells treated with Mitocytin C. In contrast, negative controls (stimulation with CM or irrelevant peptide) or naïve mice did not show any IFNg-producing cells.

Oncolytic Potential of PCVP

Figure 7:
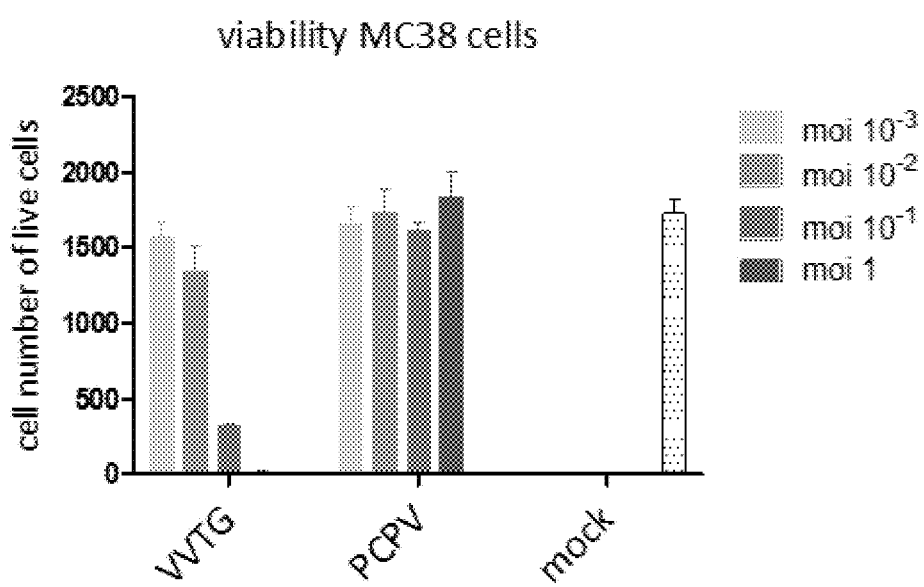
FIG. 7 illustrates the PCPV effect on viability of MC38 cells. $2×10^4$ cells were plated and infected at MOI 1, $10^{-1}$, $10^{-2}$ and $10^{-3}$ with either PCPV-GFP; VV-GFP (designated VVTG) as positive control and mock as negative control. Five days later, cells were harvested by scraping and number and proportion of living cells were determined using Trypan Blue-staining and the cell counter Vicell.

The oncolytic potential of PCPV was studied in a variety of murine and human tumor cell lines obtained from the American Type Culture Collection (ATCC, Rockville, MD) such as LoVo (ATCC® CCL-229™), HCT 116 (ATCC® CCL-247™), glioblastoma human cancer cell line U-87 MG (ATCC® HTB-14), cervix human cancer cell line HeLa (ATCC® CCL-2™) and MIA-Paca-2 (ATCC® CRL-1420™) (data not shown,) as well as the murine colon carcinoma MC38 cell line. In all these cell lines, PCPV showed a mild or no oncolytic activity Here, we show the viability of MC38 cells infected at MOI 1, $10^{-1}$, $10^{-2}$ and $10^{-3}$ with PCPV-GFP or a VV engineered to express GFP (VVTG) as positive control. Five days later, cells were harvested by scraping and number and proportion of living cells were determined using Trypan Blue-staining and the cell counter Vicell. As shown in FIG. 7, VV infection of MC38 cells strongly impaired MC38 viability (55% and 30% of cells still viable at MOI 0.1 and 1). Nineteen percent of MC38 were infected with PCPV-GFP but the virus showed no lytic effects in the infected cells (as evidenced by the same number of live cells at increasing from MOI $10^{-3}$ to 1). Mock treatment has as expected no effect on MC38 viability.

Based on these results, one may anticipate that tumor control observed with PCPV cannot be explained with oncolytic virtues of this virus in MC38 cells. Therefore, other correlates with in vivo efficacy of PCPV were studied, like cytokine/chemokine profile and tumor infiltrating lymphocytes (TILs).

Local Cytokine Profile In Vivo after Subcutaneous (sc) Application of MVAN33.1 or PCPV For local cytokine and chemokine detection, mice were injected in both flanks applying $5 \cdot 10^5$ pfu/flank. Two skin samples per mouse were cut into small pieces in 500 µl PBS in C-type tubes (Miltenyi Biotec), and mechanically dissociated (GentleMACS; Miltenyi Biotec). After centrifugation at 300 g, supernatants were transferred in Eppendorf tubes and centrifuged at 18000 g in the cold. Cleared supernatant was analyzed with Procartaplex mouse chemokine and cytokine multiplex kits using a MagPix device according to the manufacturer's recommendations.

Figure 8:
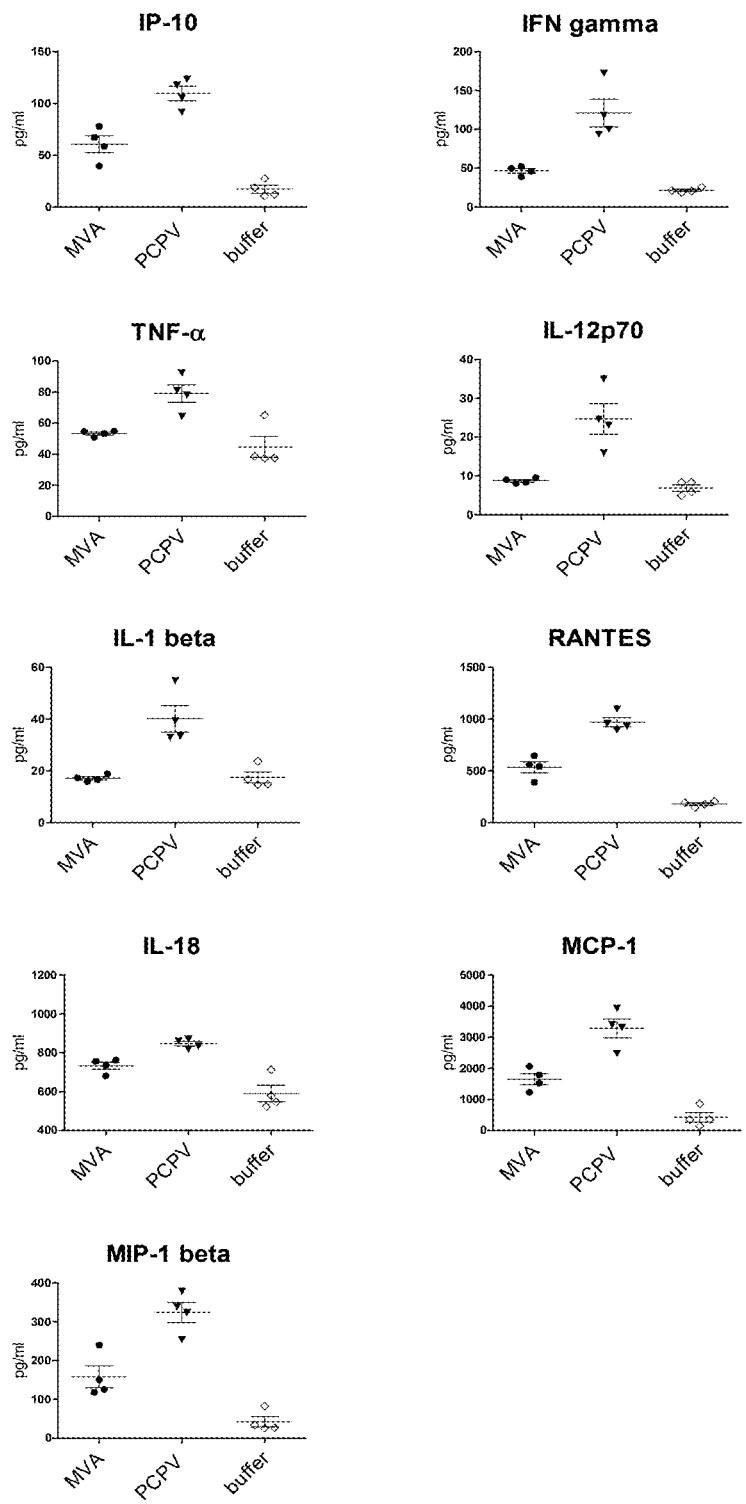
FIG. 8 illustrates the local cytokine and chemokine profile after sc injection of PCPV or MVA or buffer (as negative controls). $5×10^5$ pfu of virus/flank were injected sc in both shaved flanks of four mice per group. For each mouse, skin from both flanks was taken after 16 hours, and mechanically dissociated preserving the cells (liberation of interstitial/extracellular analytes). After centrifugation at 300 g, supernatants were transferred in Eppendorf tubes and centrifuged at 18000 g in the cold. Cleared supernatant was analyzed with Procartaplex mouse chemokine and cytokine multiplex kits using a MagPix device according to the manufacturer's recommendations.

Four mice per group were analyzed. Profiles obtained after injection of MVA and PCPV were compared to buffer (negative control). In general, each analyte was secreted to higher extents after injection of PCPV than after MVA or buffer. As expected treatment with buffer had no effect on the cytokine secretion. Surprisingly, compared to MVAN33.1, PCPV induced significantly higher local levels of IP-10, IFN-gamma, TNF-alpha, IL-12, IL-1 beta, RANTES, IL-18, MCP-1 and MIP1-beta (as illustrated in FIG. 8) as well as of IL-4, GM-CSF, MIP-1alpha, Eotaxin, IL-6, GRO-alpha, MCP-3, G-CSF, M-CSF and LIF (data not shown).

Effect of PCPV on TILs in Murine MC38 Model

Mice were split into 3 groups of 6 animals. Palpable tumors grown after sc implementation of MC38 cells (palpable tumors of at least 100 mm$^3$) were injected intratumorally 9 days after tumor cell implantation with $1 \times 10^7$ pfu of recombinant PCPV or MVA (both viruses encode HPV16E7m, an antigen irrelevant for this tumor model) or buffer (negative control). The day after virus injection, mice were sacrificed, tumors were isolated, enzymatically dissociated (Miltenyi products: tumor dissociation kit, C tube, Gentle Macs program: Tumors m_imp tumor 02 followed by 40 min at 37° C. under agitation terminated with program m_imptumor_03 twice) and TILs were enriched. After filtration of resulting cell suspension (70 µm pores) and erythrocyte lysis (BD PharmLyse, 5 min), CD45+ cells were enriched using magnetic beads technology (Miltenyi products: CD45 TILs MicroBeads, separation on MultiMAVS Cell24, program: prog POSSEL+bloc 24). Subpopulations within the CD45+ enriched cells were identified by flow cytometry according to Brauner et al. (AACR 2017 poster abstract No 1672). The percentage of neutrophils was detected in the population of CD11b+ Ly6G+ CD45+ cells. TAMs were identified as CD11c– subpopulation within Ly6G– CD11b+ cells. Various subpopulations were stratified with MHC II and Ly6C. "TAM C" according to Brauner et al, were characterized as MHC II$^{lo}$ and Ly6C.

Figure 9:
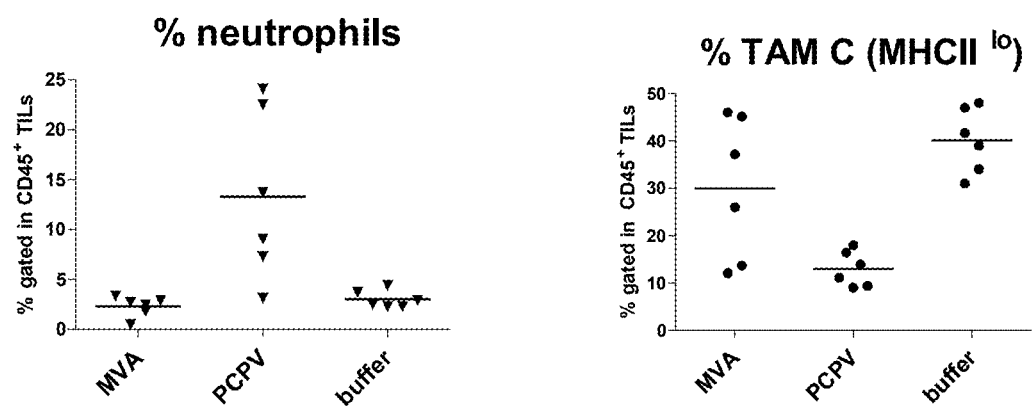
FIG. 9 illustrates the effect of PCPV on TIL composition. The percentage of neutrophils was detected in the population of CD11 b$^+$ Ly6G$^+$ CD45$^+$ cells (A). TAMs were identified as CD11c– subpopulation within Ly6G$^-$ CD11 b$^+$ cells. Various subpopulations were stratified with MHC II and Ly6C. "TAM C" according to Brauner et al, were characterized as MHC II$^{lo}$ and Ly6C$^+$.

FIG. 9 illustrates the ability of PCPV to enhance the percentage of neutrophils in growing tumors (9A) while decreasing the percentage of TAM C population (9B). These results could be indicative of PCPV-mediated tumor control.

There is also growing appreciation of neutrophil heterogeneity in cancer, with distinct neutrophil populations promoting cancer control or progression (reviewed in Singel and Segal, 2016, Immunol Rev. 273: 329-43). A further characterization of subpopulations may be useful, as well as their impact on CTL population and functions.

Concerning TAM C macrophages (MHC $II^{lo}$), Movahedi et al. (2010, Cancer Res70: 5728-39) describe different TAM subsets in mouse mammary tumors. MHC $II^{lo}$ TAMS are more of a M2-like phenotype, are enriched in hypoxic tumor areas, have superior proangiogenic activity in vivo, and increased in numbers as tumors progressed. Reducing this population could be indicative for a better prognostic of tumor control.

Example 4: In Vivo Immunogenicity Studies Using PCPV Expressing HPV-E7m

ELISPOT Analysis

The immunogenicity induced by PCPV vaccine vector was assessed by ELISPOT and compared to MVA, the animals were divided in 4 groups of 6 mice, one treated with PCPV encoding HPV16 E7mut, one with its MVA counterpart (MVA-HPV16E7mut), one treated with empty MVA (MVA N33) and a negative group receiving buffer. $1 \times 10^5$ pfu of virus were injected intravenously at day 1 and day 8 into C57BL/6 mice. One week after the second immunization (at day 15), mice were sacrificed and spleens and lungs isolated, Spleens of all mice from one group were pooled for ELISPOT analyses. Lungs were either pooled (exp ICS24) or tested individually (exp ICS28) for antigen-specific CD8+ T cells by intracellular cytokine staining. Antigen-specificity was probed in both tests with the HPV16E7-specific peptide R9F, the MVA-specific peptide T8V, and the irrelevant peptides I8L or K9i-3C CTRL.

ELISPOT analysis for antigen-specific IFN-gamma producing splenocytes was carried out according to standard protocol.

Plate Preparation

Plates (Millipore, MSIPS4W10) were pre-treated 1 minute with Ethanol 35% (15 µl/well) and washed five times with sterile water (200 µl/well). Wells were coated with 100 µl of 15 µg/ml anti-mouse IFNg antibody (Mabtech, AN18, 3321-3-1000; diluted in PBS) and incubated overnight or over week-end at +4° C. The day of the experiment, plates were washed five times with sterile PBS (200 µL/well) and saturated for at least 1 h at 37° C. with complete medium (CM 200 µL/well).

Sample Preparation

Ex vivo Elispots were performed with fresh splenic lymphocytes. For each experiment, spleens from 5 animals of each group were collected and pooled. Spleens were collected in 4 mL of complete medium (CM; X-Vivo, Lonza BE04-380Q) and then crushed with a syringe plunger through a 70 µm cell strainer in a 6-well plate. Splenocyte suspension obtained was diluted 2-fold in CM, laid over 4 mL of Lympholyte®-M separation cell media (Cedarlane, ref: CL5035) and centrifuged for 20 minutes at 1500 g at room temperature. The interphase containing lymphocytes was collected and washed twice in 10 mL of PBS (centrifugation 5 minutes at 400 g at room temperature). Lymphocytes were resuspended in 2 mL of red blood cell (RBC) lysis buffer (BD PharmLyse, BD BioScience, ref 555899) and incubated for 5 to 15 minutes at room temperature to lyse red blood cells. After one wash step in CM (centrifugation 5 minutes at 400 g at room temperature) lymphocytes were resuspended in 10 mL of CM and counted using the «Z2 Coulter particle count and size analyzer» of Beckman Coulter. Cell concentration was adjusted to $1 \times 10^7$ cells per mL with CM.

Assay

First, saturating medium was removed by emptying the plates and 50 µL CM was added in all wells. 50 µL of each peptide solution at 4 µg/mL in CM or 50 µL of CM (negative control) were added into the relevant wells (according to a previously defined pipetting scheme; each condition was tested in quadruplicate). As positive control, 50 µL of 20 µg/mL of Concanavalin A (ConA) were added into predefined wells. Secondly, 100 µL of each lymphocyte suspension ($1 \times 10^6$ cells) were added into the wells (with the exception of T8V wells where only $3 \times 10^5$ cells were added) and plates were incubated for 18 h to 20 h at 37° C. in 5% $CO_2$.

The following day, cells were removed by emptying the plates, plates were washed 5 times with PBS (200 µL/well) and biotinylated anti-mouse IFNg monoclonal antibody (Mabtech, R4-6A2, 3321-6-1000; 1 µg/mL final concentration in PBS 0.5% FCS) was distributed in each well (100 µL/well). Plates were incubated for 2 hours at room temperature, then washed five times with PBS and Extravidin-Phosphatase alkaline (SIGMA, E236, 1/5000e in PBS 0.5% FCS) was distributed in each well (100 µL/well). Plates were again incubated for 1 hour at room temperature, washed five times with PBS and 100p1 of BCIP/NBT substrate solution (BCIP/NBT tablets, SIGMA, B5655; 0.45 µM filtered) were distributed in each well. Plates were incubated at room temperature, in darkness, until distinct spots were seen in positive wells (for 5 to 10 minutes). Color development was stopped by emptying the plates and extensive washings in with tap water. Plates were left in darkness without lid until they dried for at least 1 h at room temperature.

Data Acquisition

Spots were counted with an ELISpot reader (CTL Immunoqpot reader, S5UV). A quality control was performed for each well to ensure that the counts provided by the ELISpot reader match with the reality of the picture. Results were expressed for each quadruplicate as the mean number of spot forming units (sfu) per $1 \times 10^6$ splenic lymphocytes. Positivity was determined by the R script (livelink Biostat).

Results

Figure 10:
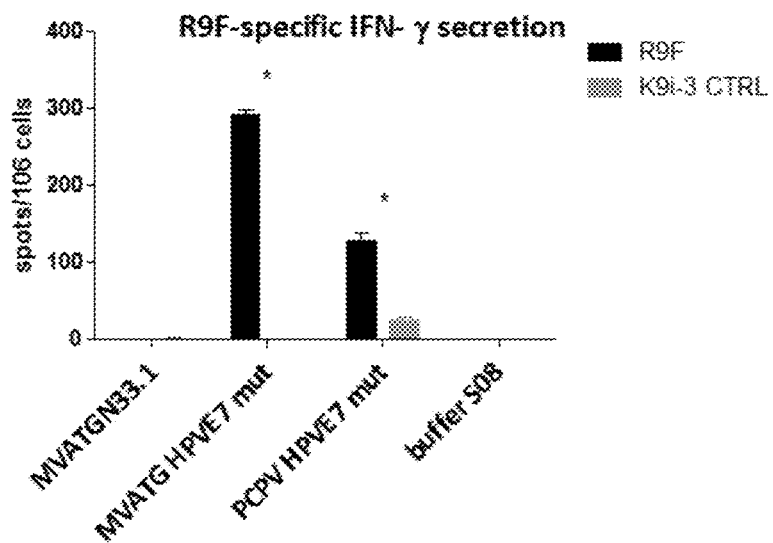
FIG. 10 illustrates (A) the generation of HPV16 E7-specific T cells in pooled spleens (ELISPOT) after stimulation with R9F peptide, (B) the generation of MVA-specific T cells after stimulation with T8V, (C) the appearance of the CD3$^{dim}$CD8$^{dim}$ T cell population in pooled lungs of mice repeatedly treated intravenously (iv) with the indicated virus and (D) the generation of HPV-16 E7-specific T cells in pooled lungs within the CD3$^{dim}$CD8$^{dim}$ T cell population.
Figure 10:
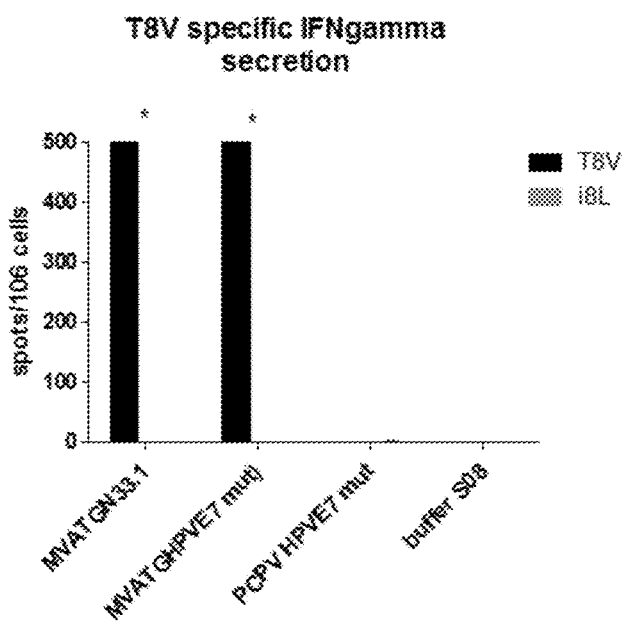
Figure 10:
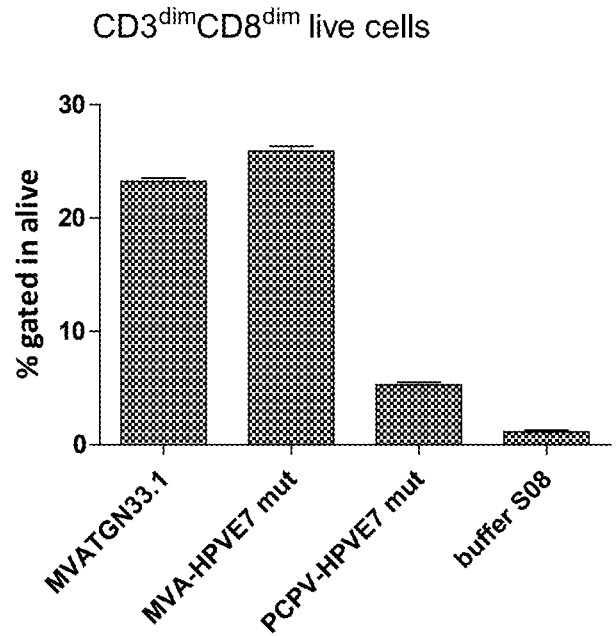
Figure 10:
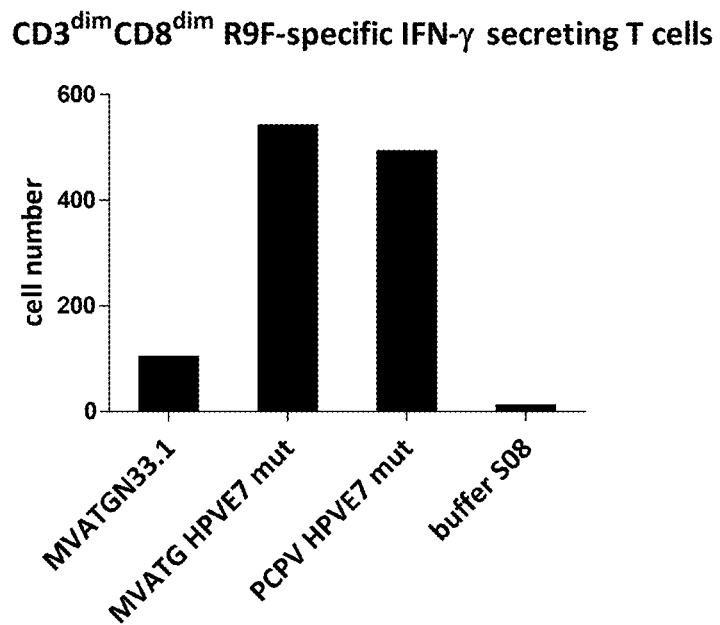

Splenocytes taken from the group of animals treated with HPV16E7m-encoding PCPV and MVA showed R9F specific IFNγ secretion as illustrated in FIG. 10A, bringing to light the capacity of the two recombinant viruses to elicit a specific immune response directed to the encoded antigen. On the other hand, no IFNγ secretion could be detected after administration of the empty MVA or buffer or following stimulation with the irrelevant peptide K9i-3. On the other hand, only MVA vectors (either empty and recombinant MVA) reply following stimulation with the MVA-specific peptide T8V (FIG. 10B).

ICS Analysis on Pooled Lung Samples

The lungs of immunized mice were either pooled (ICS 024) or treated individually (ICS 028), as described in Remy-Ziller et al. (2018, Hum Vaccin Immunother. 14: 140-5). First, lungs were enzymatically and mechanically dissociated (Miltenyi products: tumor dissociation kit, C-tubes and GentleMacs). Two×$10^6$ cells were stimulated ex vivo in 150 µl TexMACS medium (Miltenyi) in the presence of 1 µg anti CD28 (abcam), and either the HPV16E7-specific peptide R9F, the MVA-specific peptide T8V, or the irrelevant peptide I8L. After five hours of incubation in the presence of Brefeldin, cells were analysed by flow cytometry using anti CD3 and anti CD8 antibodies. After permeabilization (Cytofix/Cytoperm, BD Bioscience), activation was assessed by intracellular staining with anti-IFN-gamma-FITC (clone XMG1.2, BD Pharmingen) or its isotype control. A lymphocyte subpopulation was defined as $CD3^{dim}CD8^{dim}$ subpopulation comprising short-lived effecter cells and early effector cells. Dot blot analysis shows that two injections of recombinant MVA or PCPV lead to the appearance of a $CD3^{dim}CD8^{dim}$ population (as described in Remy-Ziller et al, 2018, Hum Vaccin Immunother. 14: 140-5) composed of effector CD8+ T cells (data not shown). The extent to which this population was expanded was superior for MVA than PCPV FIG. 10C). Nevertheless, comparable numbers of R9F-specific T cells were detected in these subpopulations after injections of HPV16 E7m-encoding PCPV or MVA as shown in FIG. 10D. In other terms, the absolute number of R9F-specific IFN-gamma-secreting cells was comparable in animals administered with HPV16E7m-encoding PCPV and MVA, even though the overall number of $CD3^{dim}CD8^{dim}$ cells induced by PCPV was lower. This suggests that the fold-induction of HPV16 E7-specific CD8+ T cells was higher after vaccination with the PCPV vector than with the MVA vector.

Figure 11:
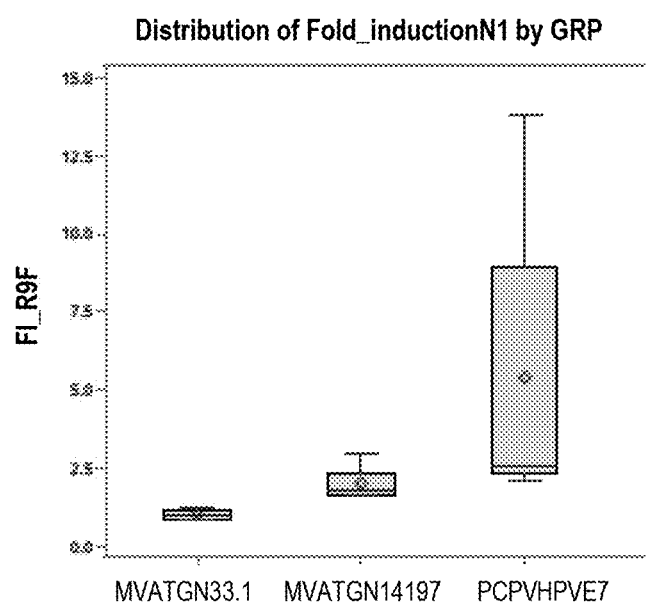
FIG. 11 illustrates the fold induction (specific peptide versus control peptide) of the appearance of HPV16 E7-specific T cells within the CD3$^{dim}$CD8$^{dim}$ T cell population measured by ICS upon infection with an empty MVA (MVATGN33.1), HPV16E7-encoding MVA (MVATG14197) and HPV16E7-encoding PCPV.

Individual lungs of mice vaccinated with MVAN33.1, HPV16E7-encoding MVA and HPV16E7-encoding PCPV (i.e; non-oncogenic version thereof) were analyzed in terms of fold increase of R9F-specific IFN-gamma-secreting CD8+ T cells within the $CD3^{dim}CD8^{dim}$ population. As shown in FIG. 11, a significant higher (fold increase) number of counts was found in HPVE7 PCPV-treated group compared to HPVE7 MVA-treated group.

All together, these data showed that like MVA-E7, PCPV-E7 induced a strong cellular response (ELISPOT on splenocytes, and frequency of antigen-specific short-lived effector cells), but PCPV-E7 displayed a different profile at the site of injection, with increased levels of pro-immune cytokines including IP-10, IFN-gamma, GM-CSF, IL-18, MIP-1 alpha, MIP-1 beta, IL-12 and IL-6. When injected intratumorally into fast growing MC-38 tumors, PCPV led to tumor control. Analysis of tumors infiltrates showed that PCPV treatment led to higher levels of neutrophils and decreased frequency of $MHCII^{lo}$ (M2) TAMs.

In conclusion, our data demonstrate that PCPV might display better properties than current viral vectors, in terms of local response and priming activity, of ability to induce effector T cells and to reshape the tumor infiltration profiles. Although many gene differences compared to other poxviruses, PCPV has the capacity to encode and deliver large genetic payload, which be useful for designing advanced anti-tumor vaccines.

Heterologous Prime Boost (PCPV/MVA)

It was published that patients with PCPV infection do not develop immunity to vaccinia/MVA and vice versa (Friedman-Kien et al., 1963, Science 140: 1335-6). Combination treatment with MVA-HPV16E7 and PCPV-HPV16E7 was thus studied in TC1 tumor model.

To this, HPV16E7-positive TC1 cells were subcutaneously implanted in the flank of C57BL/6 mice. After 14 days, tumor-bearing mice were randomized (10 mice per group), and intratumorally injected with $1 \times 10^6$ pfu of MVA-HPV16E7 or PCPV-HPV16E7. One week later, boost was carried out by intravenous injection with $1 \times 10^6$ pfu of PCPV-HPV16E7 or MVA-HPV16E7. Tumor growth and survival were followed over time in mice treated with homologous MVA/MVA and heterologous MVA/PCPV and PCPV/MVA settings or with buffer under the same conditions (intratumoral prime and iv boost) as negative control.

Figure 14:
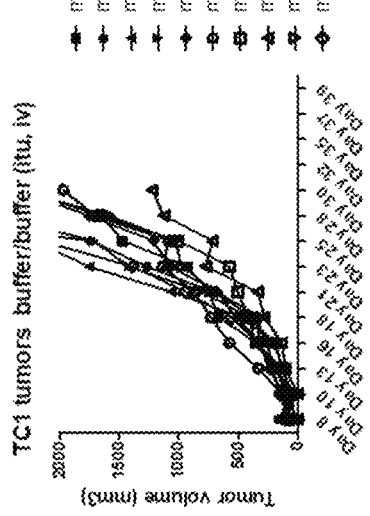
FIG. 14 illustrates a tumor control experiment in TC1-bearing C57BL/6 mice according to a prime/boost setting. TC1 cells were subcutaneously implanted in the flank of C57BL/6 mice. After 14 days, tumor-bearing mice were randomized (10 mice per group), and intratumorally injected with $1\cdot10^6$ pfu of MVA-HPV16E7 (A and B) or PCPV-HPV16E7 (C) or buffer (D) (priming injection). One week later, mice were boosted with intravenous injection of $1\times10^6$ pfu of the counterpart virus, i.e. PCPV-HPV16E7 (D) or MVA-HPV16E7 (A and C) or buffer (B in the buffer primed mice). Tumor growth were followed overtime.
Figure 14:
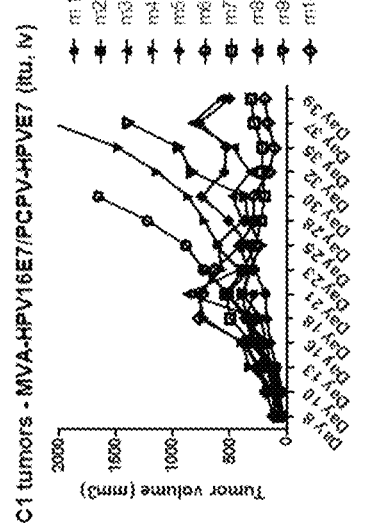
Figure 14:
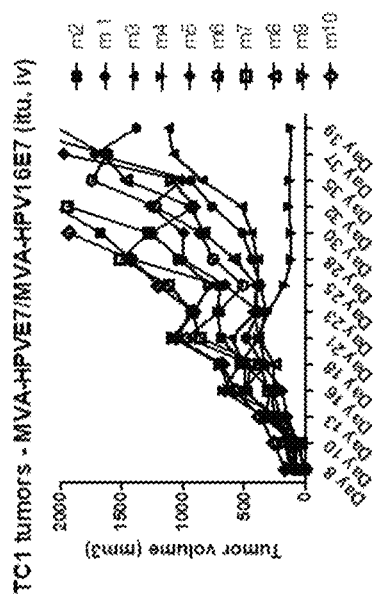
Figure 14:
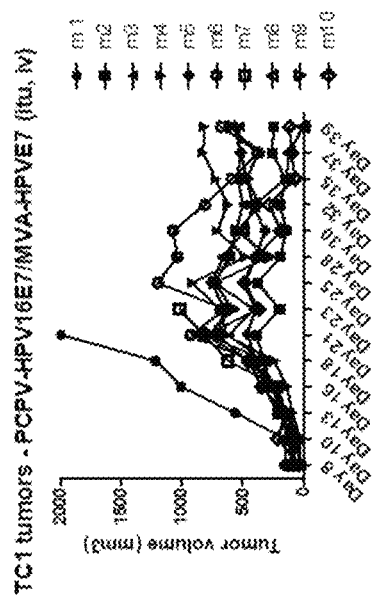

As illustrated in FIG. 14, heterologous treatments resulted in better tumor control compared to treatment with homologous MVA-HPV16E7 prime boost. Interestingly, both MVA prime/PCPV boost or PCPV prime/MVA boost produced a decline in tumor growth with respect to MVA prime/MVA boost group although PCPV prime/MVA boost trends to better control tumor growth (tumor control in a higher number of mice as shown in FIG. 14C). As expected, tumor grew quite rapidly in buffer treated animals.

Example 5: Combo Treatment of PCPV with an ICI (Immune Checkpoint Inhibitor)

The effect of combining PCPV treatment with systemic ICI treatment was evaluated in the MC38-tumor model. The rat anti mPD-1 (m for mouse) antibody RMP1-14 (commercially available from BioXcell) was chosen. This antibody was shown to block the interaction of mPD1 with its ligands (Yamazaki et al., 2005, J. Immunol. 175(3): 1586-92).

On day 1 (D1), the colon carcinoma cell line MC38 ($2 \times 10^6$ cells) was injected subcutaneously (sc) in the right flank of syngeneic C57BL/6 mice shaved 2 days before. The injection site was labeled with a permanent marker. The same day, four-time less MC38 cells ($5 \times 10^5$) were injected sc in the left flank. One $10^7$ pfu of PCPV (PCPTG19178) or VV virus (VVTG5095), both encoding HPV16E7m (irrelevant for the MC38 model), or buffer (S08) were injected intratumorally (it) at the cell line injection site on the right side (day 2) and later in the emerging right tumors (days 9 and 16). On the other hand, 200 μg of anti-mPD-1 (RMP1-14) was injected intra peritoneally (ip) at days 5, 9 and 16. Tumor growth of right (injected) and left tumors and survival were followed over time.

Altogether, the animals were divided in 6 groups of 13 mice, respectively:
 a control group receiving S08 buffer (3 it injections at days 2, 9 and 16),
 a group of mice treated with the E7-expressing PCPV virus (3 it injections of $10^7$ pfu of PCPTG19178 at days 2, 9 and 16),
 a group of mice treated with the E7-expressing oncolytic VV virus (3 it injections of $10^7$ pfu of VVTG5095 at days 2, 9 and 16),
 a group of mice treated with the anti PD1 antibody (3 ip injections of RMP1-14 antibody at days 5, 9 and 16,
 a group receiving both the E7-expressing PCPV virus and the anti PD1 antibody (3 it injections of $10^7$ pfu of PCPTG19178 at days 2, 9 and 16 and 3 ip injections of RMP1-14 antibody at days 5, 9 and 16), and
 a group receiving both the E7-expressing VV oncolytic virus and the anti PD1 antibody (3 it injections of $10^7$ pfu of VVTG5095 at days 2, 9 and 16 and 3 ip injections of RMP1-14 antibody at days 5, 9 and 16).

Figure 15:
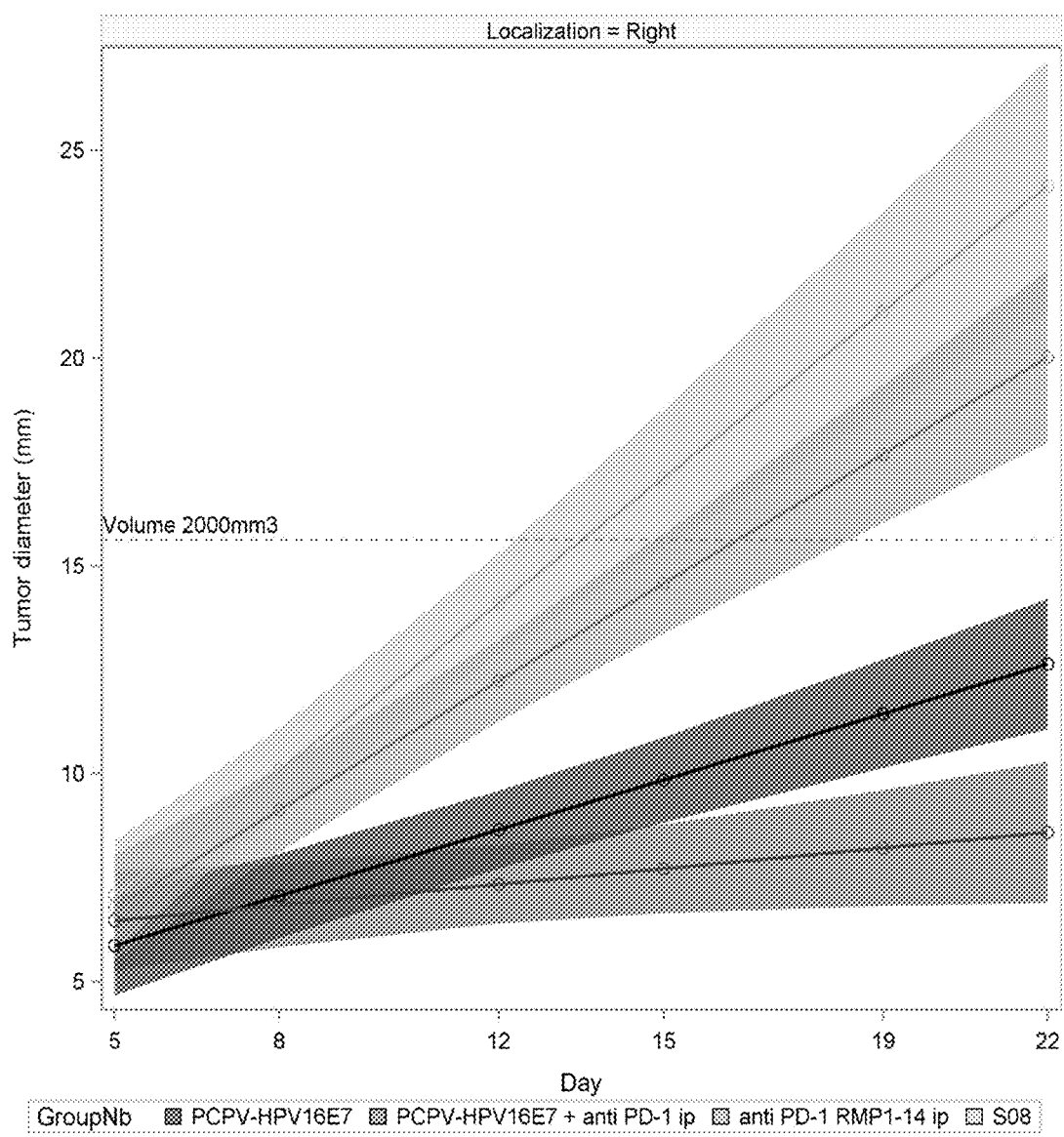
FIG. 15 illustrates a tumor control experiment in MC38-bearing mice upon intratumoral injection of $1\times10^7$ pfu of PCPV (A) or VV (B) either as stand-alone (dark grey) or in combination with the murine anti-PD1 (intraperitoneal injection) (medium grey). Control group received S08 buffer (lightest grey) or anti-PD1 antibody alone (light grey). Each group comprises 13 mice.
Figure 15:
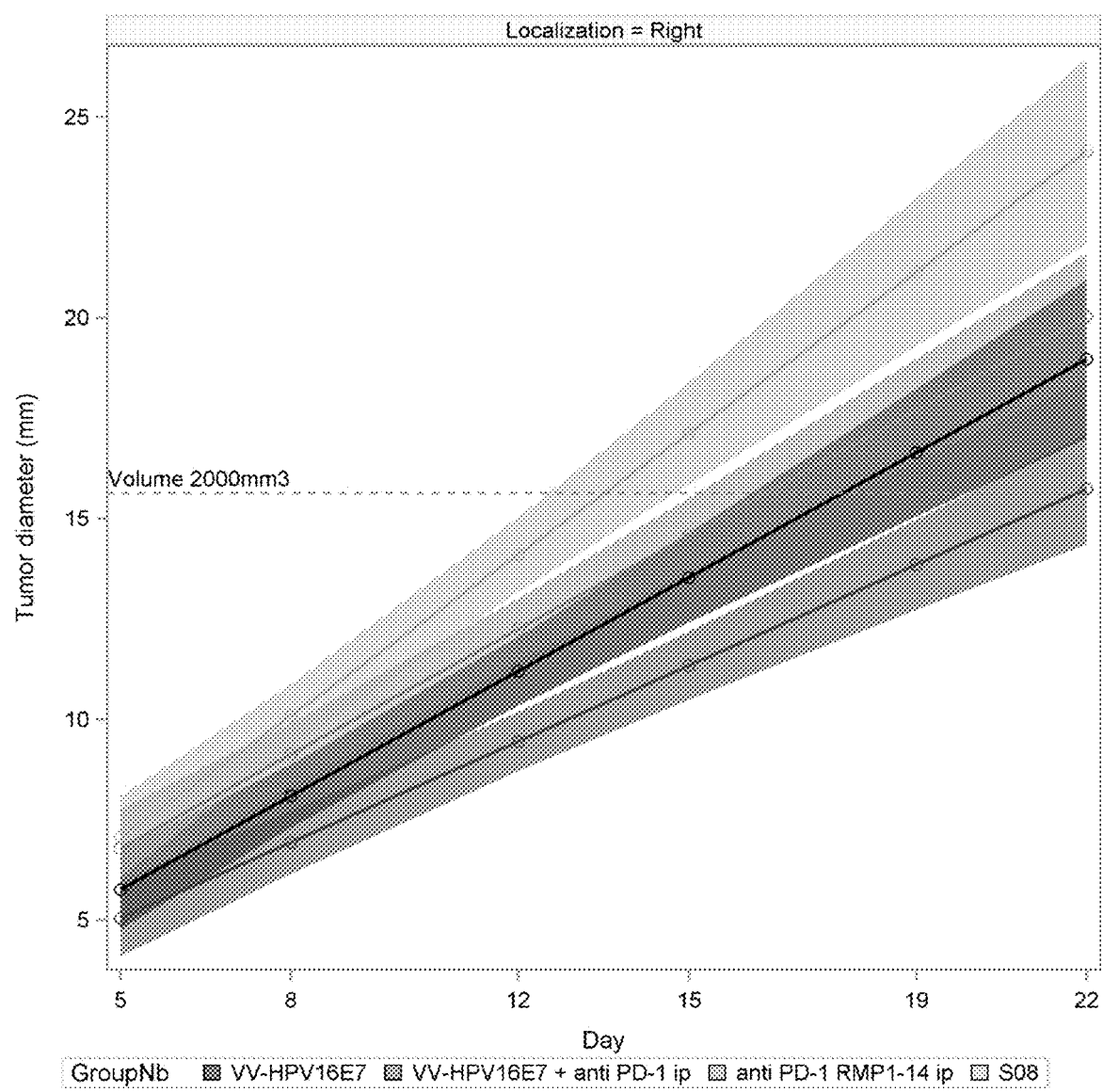

FIG. 15 shows diameter evolution of the tumors implanted on the right flanks in the groups of mice treated with PCPV (A) or VV (B) either as stand alone or in combination with the murine anti-PD1. More specifically, tumors grew rapidly in the control group (S08) going beyond 2000 mm³ on average as soon as D13 whereas treatment with anti-mPD1 allowed to postpone the average 2000 mm³ volume of some days (D16). As illustrated in FIG. 15B, the same tendency was observed following treatment with the oncolytic VVTG5095 (dark grey). But tumor growth was controlled in mice treated with VVTG5095 and anti-mPD1 in combination (middle grey) where average 2000 mm³ volume was obtained at D22. In contrast, as shown in FIG. 15A, tumor growth is significantly delayed following treatment with PCPV virus (dark grey) where the average tumor volume was well below 2000 mm³ at D22 and even more in the combo group (medium grey) receiving both PCPTG19178 and anti-PD1. Notably, in combo PCPV-HPV16E7+anti PD-1 group, difference in tumor size was found significant versus the tumor sizes obtained in the three other groups PCPV-HPV16E7, anti PD-1 and S08.

In contralateral tumors (left flank), treatment with the anti-mPD1 antibody delayed tumor progression. A significant tumor size reduction was found in anti-PD1 group versus the other groups (data not shown).

For Survival analysis (data not shown), a significant higher OS was found in both PCPV-HPV16E7 group and PCPV-HPV16E7+anti PD-1 combo group versus S08 buffer group (adjusted p-values were both 0.036). Mean survival differences were respectively 4.4 days and 3.4 days. A significant higher OS was also found in VV-HPV16E7+anti PD-1 combo group versus VV-HPV16E7 and control groups (adjusted p-values were both 0.040 and 0.004). Mean survival differences were respectively 2.9 days and 3.6 days.

These results highlight that combining a recombinant PCPV with an ICI such as anti-PD1 allows to strengthen the anti-tumor protection.

Example 6: Effect of Bovine Popular Stomatitis Virus

The Parapoxvirus genus comprises distinct members including the ORF virus, PCPV and the bovine papular stomatitis virus (BPSV), all can cause infections of ruminants and their handlers (Zhao et al, 2013, J Virol Methods, 194:229-34). PAPV infection in humans induces vigorous and short-lived cell-mediated immune response and a poor and short-lived humoral response, about 8-12% of individuals have second infections handlers (Zhao et al., 2013, J Virol Methods, 194:229-34).

Another member of Parapoxvirus genus, (BPSV) was tested for its ability to induce the secretion of IFN alpha in PBMCs obtained from 2 different donors and compared to MVA and PCPV (see Example 1). Fresh PBMCs were isolated, incubated overnight (resting) and infected next day with the virus at MOI 0.3. A CpG type TLR9 ligand (ODN2216 obtained from Invivogen) was added as a control for pDC, B cell-mediated secretion of IFN-alpha. Supernatants were taken 2, 4, 6, 16 or 24 h after infection, IFN-alpha in the supernatant was quantified by Luminex technology as described above.

Figure 16:
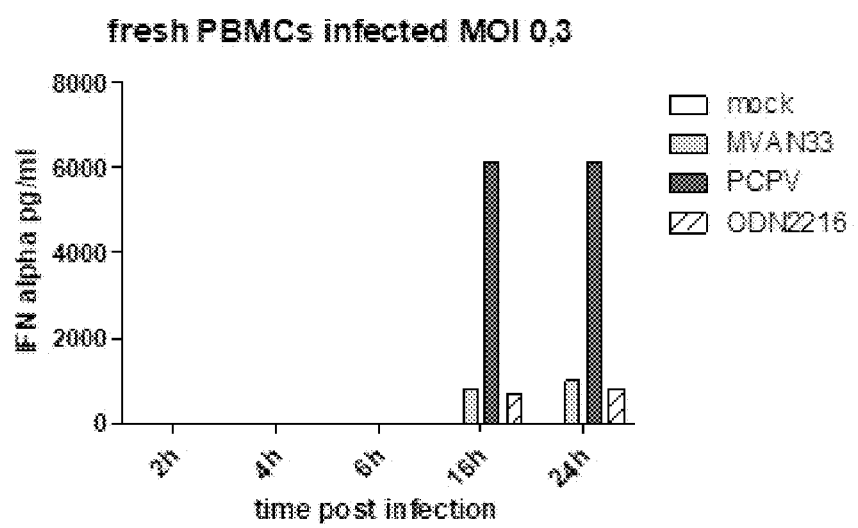
FIG. 16 illustrates IFN-alpha secretion in PBMCs obtained from a representative donor and infected with MVA, PCPV or BPSV at MOI 0.3. Mock represents the negative control and ODN2216 a CpG type TLR9 ligand as a control of immunostimulatory effect.

As shown in FIG. 16, BPSV-infected PBMCs as PCPV-infected PBMCs induced the secretion of very high levels of IFN-alpha at 16 and 24 h post cell infection. The secreted IFN-alpha levels in both cases were well above the moderate secretion levels of IFN-alpha observed upon MVA infection confirming the results obtained in Example 1 and above the ODN2216 control.

In conclusion, BPSV showed similar effects as PCPV, i.e. strong increase of secreted IFN-alpha in supernatant of PBMCs obtained from various donors.

BIBLIOGRAPHIC REFERENCES

Brauner et al. AACR 2017 poster abstract No 1672;
Carpentier et al., 2003, Frontiers in Bioscience 8, e115-127;
Carpentier et al., 2006, Neuro-Oncology 8(1): 60-6;
Cattaneo and Russell, 2017, PLOS Pathogens doi:10.1371/journalppat.1006190;
Chakrabarti et al., 1997, Biotechniques 23: 1094-7;
Chan, 2008, Eur. J. Immunol. 38, 2964-2968;
Choi et al. (2017, Surgery, doi 10.1016/j.surg.2017.09.030;
Claudepierre et al., 2014, J. Virol. 88(10): 5242-55;
Coligan et al. (1992 and 1994, Current Protocols in Immunology; ed J Wiley & Sons Inc, National Institute of Health;
Erbs et al., 2008, Cancer Gene Ther. 15(1): 18-28;
Evans et al. 2004, J Pharm Sci. 93:2458-75;
Fend et al., 2014, Cancer Immunol. Res. 2, 1163-74;
Friedman-Kien et al., 1963, Science 140: 1335-6;
Gomez et al., 2013 expert Rev Vaccines 12(12): 1395-1416;
Hammond et al, 1997, J. Virol Methods 66: 135-8;
Hautaniemi et al., 2010, J. Gen. Virol. 91: 1560-76;
Kaufman et al., 2015, Nature Reviews Drug Discovery 14: 642-661;
Kern et al., 1990, Gene, 88: 149-57
Kumar and Boyle, 1990, Virology 179: 151-8;
Laidlaw and Skinner, 2004; J. Gen. Virol., 85: 305-22;
Mia et al., 2014, Scand. J. Immunol. 79(5): 305-14;
Movahedi et al., 2010, Cancer Res70: 5728-39;
Needleman and Wunsch. J. Mol. Biol. 48,443-453, 1970;
Parker et al., 2016, Nat Rev Cancer 16(3): 131-44;
Perez and Brady, 1992, Principles and Practice of Radiation Oncology, 2nd Ed. JB Lippincott Co;
Quoix et al., 2011, The Lancet Oncology 12(12): 1125-33;
Remy-Ziller et al., 2018, Hum Vaccin Immunother. 14: 140-5;
Remington: The Science and Practice of Pharmacy, A. Gennaro, Lippincott, Williams&Wilkins;
Rintoul et al., 2012, Mol. Ther. 20(6): 1148-57;
J. R. Robinson in "Sustained and Controlled Release Drug Delivery Systems", ed., Marcel Dekker, Inc., New York, 1978;
Rooij et al., 2010, Vaccine 28(7): 1808-13;
Rziha et al., 2000, J. Biotechnol. 83(1-2): 137-145;
Schulze et al., 2009, Vet Microbiol. 137: 260-7);
Scott-Algara et al., 2010 PLOS One 5(1), e8761;
Shaul and Fridlender, 2017, J. Leuko. Biol. 102(2): 343-9;
Singel and Segal, 2016, Immunol Rev. 273: 329-43
Tikkanen et al., 2004, J. Gen. Virol. 85: 1413-8
Von Buttlar et al., 2014, PLOS One 9(8): e106188
Wozniak et al., 2012, BMC Immunology, 13:65
Yamazaki et al., 2005, J. Immunol. 175(3): 1586-92
Yuan et al, 2015, Nature, Scientific Reports
Zhao et al, 2013, J Virol Methods, 194:229-34
Zhou et al., 2006, Blood 107, 2461-2469
Zitvogel et al., 2015, Nat Rev Immunol. 15(7): 405-14
WO92/07000
WO96/16183
WO97/32029
WO97/37031
WO98/04727
WO98/37095
WO99/03885
WO01/23001
WO03/053463
WO2005/07857
WO2006/005529
WO2006/085082
WO2006/93924
WO2007/056847
WO2007/147528
WO2008/092854
WO2008/114021

WO2009/065546
WO2009/53937
WO2012/01145
WO2013/007772
WO2014/053571
WO2016/087457
EP 463 756
EP998568
EP 1 162 982
U.S. Pat. No. 5,250,534
U.S. Pat. No. 5,861,381
U.S. Pat. No. 6,054,438
U.S. Pat. No. 6,365,393;
U.S. Pat. No. 6,469,012
U.S. Pat. No. 7,108,844
U.S. Pat. No. 7,456,009
U.S. Pat. No. 7,700,569
US2003-0013076
US2007-0161085

The invention claimed is:

1. A vaccine composition comprising a therapeutically effective amount of a pseudocowpoxvirus (PCPV) and a pharmaceutically acceptable vehicle; wherein said PCPV comprises at least one foreign nucleic acid inserted in its genome; wherein said at least one foreign nucleic acid encodes a cancer antigen; and wherein the insertion site is selected from the group consisting of a non-essential viral gene, an intergenic region, a portion of the PCPV genome which does not encode gene products, and a duplicated locus.

2. The vaccine composition of claim 1, wherein said PCPV is obtained from the wild-type TJS strain as identified by ATCC reference number ATCC VR-634™ or from a virus strain of the same name or functional variants thereof.

3. The vaccine composition of claim 1, wherein said PCPV is further defective for a viral function encoded by the PCPV genome.

4. The vaccine composition of claim 1, wherein the at least one foreign nucleic acid is placed under the control of a vaccinia virus promoter selected from the group consisting of the 7.5K, H5R, 11K7.5, SE, TK, pB2R, p28, p11, and K1L promoter, synthetic promoters, and early/late chimeric promoters.

5. The vaccine composition of claim 1, wherein the at least one foreign nucleic acid is inserted in the VEGF locus.

6. The vaccine composition of claim 1, wherein said composition is formulated in individual doses comprising from approximately $10^3$ to approximately $10^{12}$ pfu of PCPV.

7. The vaccine composition of claim 1, wherein the composition is formulated for intravenous, intramuscular, subcutaneous, or intratumoral administration.

8. A method for eliciting or stimulating and/or re-orienting an immune response comprising administering the vaccine composition according to claim 1 to a subject in need thereof, in an amount sufficient to activate the subject's immunity.

9. The vaccine composition of claim 1, wherein said cancer antigen is a MUC-1 antigen, HPV antigen, or HBV antigen.

10. The vaccine composition of claim 1, wherein the PCPV further comprises at least one other foreign nucleic acid inserted in its genome.

* * * * *